（12）United States Patent
Ma et al.

(10) Patent No.: US 9,066,997 B2
(45) Date of Patent: Jun. 30, 2015

(54) SCAFFOLDS AND METHODS OF FORMING THE SAME

(75) Inventors: Peter X. Ma, Ann Arbor, MI (US); Haiyun Ma, BaoDing (CN)

(73) Assignee: The Regents of The University of Michigan, Ann Arbor, MI (US)

( * ) Notice: Subject to any disclaimer, the term of this patent is extended or adjusted under 35 U.S.C. 154(b) by 847 days.

(21) Appl. No.: 13/151,866

(22) Filed: Jun. 2, 2011

(65) Prior Publication Data

US 2011/0311746 A1    Dec. 22, 2011

Related U.S. Application Data

(60) Provisional application No. 61/350,778, filed on Jun. 2, 2010.

(51) Int. Cl.
| | |
|---|---|
| *B32B 1/08* | (2006.01) |
| *A61L 27/56* | (2006.01) |
| *B29C 35/16* | (2006.01) |
| *A61F 2/06* | (2013.01) |

(52) U.S. Cl.
CPC ............ *A61L 27/56* (2013.01); *Y10T 428/1393* (2015.01); *Y10T 428/139* (2015.01); *A61F 2/06* (2013.01); *A61F 2240/004* (2013.01)

(58) Field of Classification Search
CPC ..... A61F 2/06; A61F 2240/004; A61L 27/40; A61L 27/56; C08J 9/36; F61F 2/07; B01J 20/285; Y10S 128/12; Y10S 977/773; Y10S 977/795; Y10S 977/915

USPC .......... 428/36.9, 36.91, 36.92, 304.4, 311.11, 428/314.2, 314.4, 314.8, 315.7, 320.2; 264/28, 41, 234; 424/424, 423
See application file for complete search history.

(56) References Cited

U.S. PATENT DOCUMENTS

| | | | |
|---|---|---|---|
| 6,358,275 | B1 | 3/2002 | McIlroy et al. |
| 6,500,203 | B1 | 12/2002 | Thompson et al. |
| 6,673,285 | B2 * | 1/2004 | Ma .................. 264/49 |
| 2002/0150753 | A1 * | 10/2002 | Ma et al. ............. 428/357 |
| 2005/0107868 | A1 * | 5/2005 | Nakayama et al. .......... 623/1.39 |
| 2007/0162131 | A1 | 7/2007 | Friedman et al. |
| 2007/0293927 | A1 | 12/2007 | Frank et al. |

OTHER PUBLICATIONS

Breuer, C.K., et al., "Tissue Engineering Lamb Heart Valve Leaflets," Biotechnology & Bioengineering, 50, 1996, pp. 562-567.
Chen, V.J., et al., "Bone Regeneration on Computer-Designed Nano-Fibrous Scaffolds," Biomaterials, 27, 2006, pp. 3973-3979.

(Continued)

*Primary Examiner* — Yan Lan
(74) *Attorney, Agent, or Firm* — Dierker & Associates, P.C.

(57) ABSTRACT

Various embodiments of scaffolds are disclosed herein. In one embodiment, the scaffold includes a tubular polymeric structure, and a controlled gradient of solid-walled microtubules oriented radially or axially in the tubular polymeric structure. In another embodiment, the scaffold includes a nano-fibrous tubular polymeric structure, and an oriented and interconnected microtubular porous network formed in the nano-fibrous tubular polymeric structure. In still another embodiment, a composite scaffold is formed including a polymeric structure having an inner wall and an outer wall, and at least one electrospun layer positioned along at least one of the inner wall, or the outer wall, or in a middle of the porous polymeric structure.

8 Claims, 30 Drawing Sheets

(56) References Cited

OTHER PUBLICATIONS

Chen, V.J., et al., "Nano-Fibrous Poly(L-lactic acid) Scaffolds with Interconnected Spherical Macropores," Biomaterials, 25, 2004, pp. 2065-2073.

Hu, J., et al., "Chondrogenic and Osteogenic Differentiations of Human Bone Marrow-Derived Mesenchymal Stem Cells on a Nanofibrous Scaffold with Designed Pore Network," Biomaterials, 30, 2009, pp. 5061-5067.

Hu, J., et al., "Induction of Osteoblast Differentiation Phenotype on Poly(L-lactic acid) Nanofibrous Matrix," Biomaterials, 29, 2008, pp. 3815-3821.

Ma, P.X., et al., "Biodegradable Polymer Scaffolds with Well-Defined Interconnected Spherical Pore Network," Tissue Engineering, 7, 1, 2001, pp. 23-33.

Ma, P.X., "Biomimetic Materials for Tissue Engineering," ScienceDirect, Adv Drug Delivery Reviews, 60, 2008, pp. 184-198.

Ma, P.X., et al., "Microtubular Architecture of Biodegradable Polymer Scaffolds," J Biomed Mater Res, 56, 2001, pp. 469-477.

Ma, P.X., et al., "Synthetic Nano-Scale Fibrous Extracellular Matrix," J Biomed Mater Res, 46, 1999, pp. 60-72.

Shinoka, T., et al., "Creation of Viable Pulmonary Artery Autografts through Tissue Engineering," J of Thoracic and Cardiovascular Surgery, 115, 3, 1998, pp. 536-546.

Shinoka, T., et al., "Tissue Engineering Heart Valves: Valve Leaflet Replacement Study in a Lamb Model," Ann Thorac Surg, 60, 1995, pp. S513-S516.

Wei, G., et al., "Macroporous and Nanofibrous Polymer Scaffolds and Polymer/bone-like Apatite Composite Scaffolds Generated by Sugar Spheres," J. of Biomed Mater Res, 78A, 2006, pp. 306-315.

Wei, G., et al., "Nanostructured Biomaterials for Regeneration," Adv Funct Mater, 18, 2008, pp. 3568-3582.

Woo, K.M., et al., "Nano-Fibrous Scaffolding Architecture Selectively Enhances Protein Adsorption Contributing to Cell Attachment," J Biomed Mater Res, 67A, 2003, pp. 531-537.

Woo, K.M., "Nano-Fibrous Scaffolding Promotes Osteoblast Differentiation and Biomineralization," Biomaterials, 28, 2007, pp. 335-343.

Zhang, R., et al., "Poly($\alpha$-hydroxyl acids)/Hydroxyapatite Porous Composites for Bone-Tissue Engineering. I. Preparation and Morphology," J Biomed Mater Res 44, 1999, pp. 446-455.

International Search Report and Written Opinion for PCT/US2011/038915 dated Feb. 28, 2012 (10 pages).

\* cited by examiner

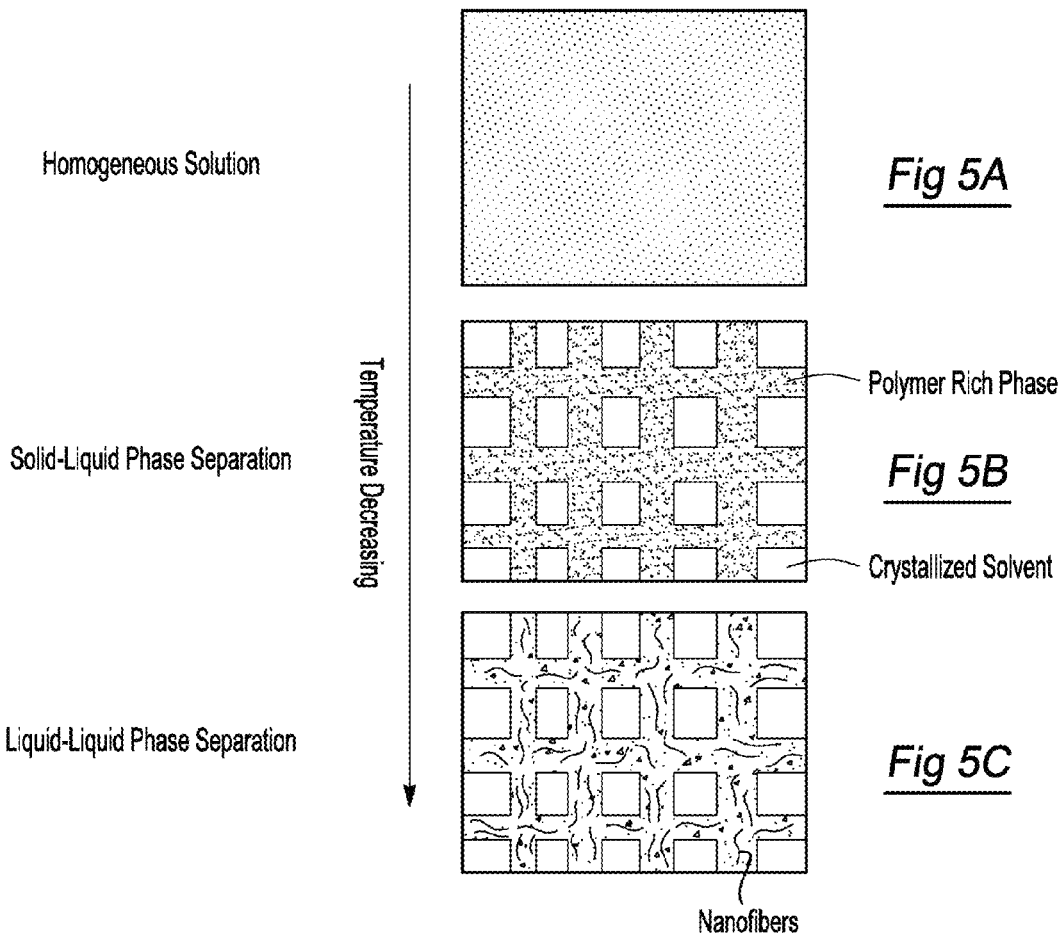
Homogeneous Solution — *Fig 5A*
Solid-Liquid Phase Separation — Polymer Rich Phase — *Fig 5B* — Crystallized Solvent
Liquid-Liquid Phase Separation — *Fig 5C* — Nanofibers
Temperature Decreasing
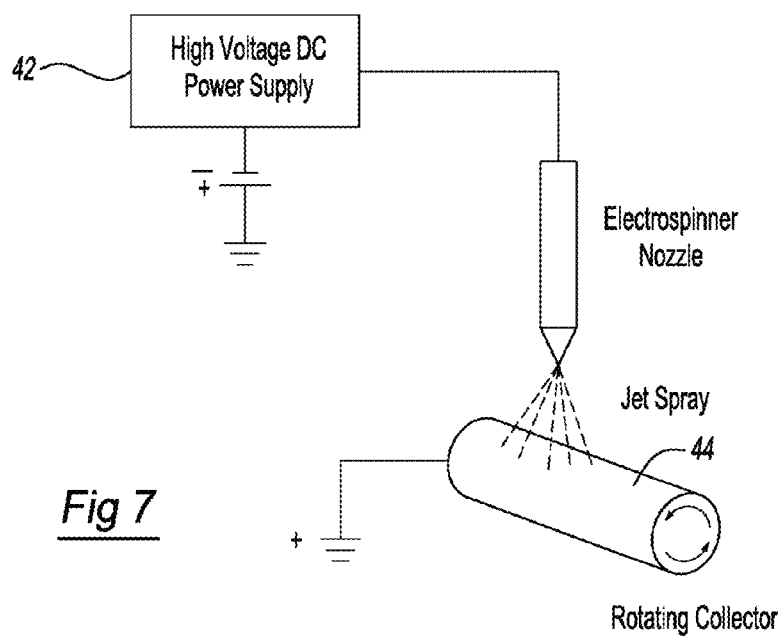
*Fig 7*

```
                              SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
ggaagggcac caccaggagt                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
tgcagccccg gacatctaag                                                   20

<210> SEQ ID NO 3
<211> LENGTH: 18
<212> TYPE: DNA
<213> ORGANISM: Artificial Sequence
<220> FEATURE:
<223> OTHER INFORMATION: Synthetic

<400> SEQUENCE: 3
ctgggacgac atggaaaa                                                     18

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
acatggctgg gacattga                                                     18

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
agagacagct tcacgagtat gag                                               23

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
cttccagctc tctttgaaag tc                                                22
```

```
<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
cctggataca gaggacatgg                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
caggtggttg tagagcgact                                              20
```

SCAFFOLDS AND METHODS OF FORMING THE SAME

CROSS-REFERENCE TO RELATED APPLICATIONS

This application claims the benefit of U.S. Patent Provisional Application Ser. No. 61/350,778, filed Jun. 2, 2010, entitled "Scaffolds and Methods of Forming the Same."

STATEMENT REGARDING FEDERALLY SPONSORED RESEARCH OR DEVELOPMENT

This invention was made with government support under Grant Nos. DE015384 and DE017689 awarded by the National Institutes of Health and National Institute of Dental and Craniofacial Research. The government has certain rights in the invention.

BACKGROUND

The present disclosure relates generally to scaffolds and method(s) of forming the same.

Cardiovascular disease is one of the leading causes of mortality in the United States. Large-diameter (i.e., inner diameter being greater than 6 mm) blood vessels have been successfully replaced with nondegradable polymeric materials such as polyethylene terephthalate (PET) and expanded polytetrafluoroethylene (ePTFE); however, these materials are not natural tissues. When these materials are used for small-diameter (i.e., inner diameter being less than 6 mm) blood vessels, poor patency may result due to thrombosis and hyperplasia. Attempts have been made to engineer biodegradable polymer scaffolds to replace the non-natural material vessels.

SUMMARY

Various examples of scaffolds are disclosed herein. In one example, the scaffold includes a tubular polymeric structure, and a controlled gradient of solid-walled microtubules oriented axially or radially in the tubular polymeric structure. In another example, the scaffold includes a nano-fibrous tubular polymeric structure, and an oriented and interconnected microtubular porous network formed in the nano-fibrous tubular polymeric structure. In still another example a composite scaffold is formed including a tubular polymeric structure having an inner wall and an outer wall, and at least one electrospun layer positioned along at least one of the inner wall or the outer wall.

Examples of methods for making the various examples of the scaffolds are also disclosed herein.

BRIEF DESCRIPTION OF THE DRAWINGS

Features and advantages of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIGS. 5A through 5C together illustrate a schematic flow diagram of an example of a method for forming an example of a nano-fibrous scaffold with interconnected microtubules;

FIG. 7 is a schematic view of an electro spinning system;

(FIGS. 15G-I) 7.5% (wt/v) PLLA/(benzene/THF) and benzene/THF (v/v)=6:4, the phase separation temperature was −20° C.;

FIGS. 20A-F are nano-fibrous porous scaffolds where A, B, and C illustrate electrospun/thermally induced phase separation (E/T), E/T/E and T/E multilayered structures, where D illustrates the interface of the E/T composite scaffold, where E illustrates the nano-fibrous structure in the TIPS layer, and where F illustrates the interface of the T/E composite scaffold, FIGS. 20M-O are solid-wall porous scaffolds where M illustrates a porous scaffold having the electrospun layer in the middle, and N and O respectively illustrate the electrospun layer and one of the porous structures of a T/E/T multilayered composite structure;

DETAILED DESCRIPTION

Examples of the scaffolds disclosed herein include structural features on multiple scales that mimic key structural features of the extracellular matrix (ECM). The scaffolds may each be fabricated with gradient structured tubules with pores or channels to facilitate cell seeding and three-dimensional blood vessel regeneration. Some examples of the scaffolds disclosed herein may be particularly suitable as blood vessel scaffolds, at least in part because they i) are formed of biocompatible and biodegradable polymers, ii) have a high porosity (i.e., 70% to 99% of the total scaffold volume) with a structure suitable for cell seeding, distribution, function and tissue regeneration, iii) have a tubular geometry which are structurally similar to the native extracellular matrix (i.e., mimicking the collagens Type I and III and elastin, which are fibers of the nano-meter dimensions), and iv) exhibit mechanical properties (e.g., compressive modulus and compressive yield strength) suitable for supporting tissue regeneration. Other embodiments of the scaffolds are configured as multi-layered structures incorporating various types of layers, which together provide, for example, integrity, mechanical strength, elasticity, suitable cell growth area, and suitable mass transport channels to the resulting composite scaffold. The various scaffolds disclosed herein may be suitable for blood vessels, heart valve tissues, skin, muscles (e.g., skeleton muscle, cardiac muscle, smooth muscle, etc/), tendons, ligaments, fat, cartilage, bone, or combinations thereof (such as bone-cartilage, bone-ligament composites, etc.).

Any of the gradient, oriented, and/or multi-layered scaffolds described herein may be formed in non-tubular forms as well, such as, for example, porous flat layered scaffolds, curved scaffolds, rod-like scaffolds, or combinations thereof. These alternate configurations may be suitable for any of the previously described applications, such as for vessels, heart valves, skin, muscles, tendons, ligaments, cartilage, bone, and especially including their transitional or interface regeneration and repair.

The scaffolds disclosed herein include a variety of features, such as solid wall tubules, fibrous wall tubules (e.g., where the walls are made up of nano-fibers), pores, channels, etc. These features may be nano-features, micro-features, macro-features and/or combinations thereof. It is to be understood that, as defined herein, nano-features are intended to include features (e.g., fibers, tubules, pores, channels, etc.) ranging in size from about $10^{-10}$ meters to about $10^{-6}$ meters; micro-features are intended to include features ranging in size from about $10^{-6}$ meters to about $10^{-3}$ meters; and macro-features are intended to include features have a size greater than or equal to $10^{-3}$ meters.

Figures 1A, 1B, 1C:
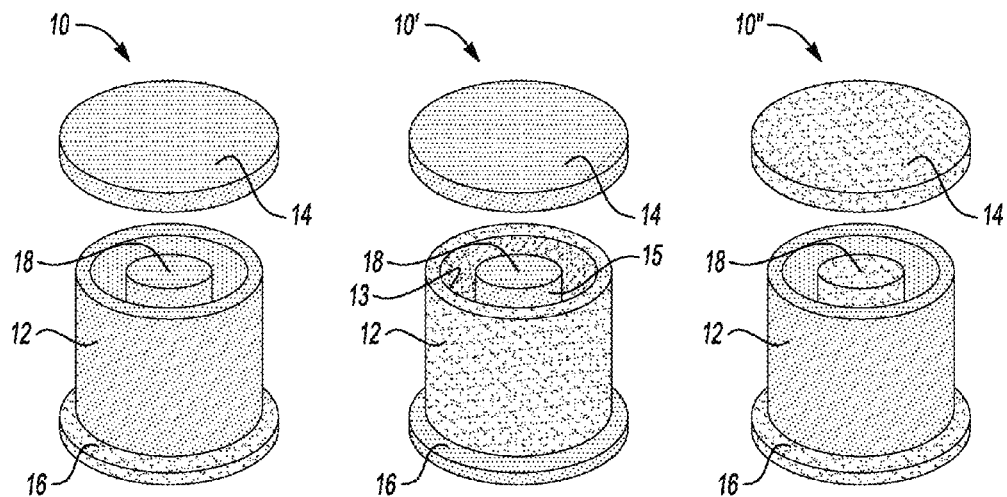
FIGS. 1A through 1C are perspective views of molds for preparing examples of the scaffolds disclosed herein.

In one example, the scaffold includes a tubular polymeric structure, and a controlled gradient of solid-walled microtubules oriented radially or axially in the tubular polymeric structure. These examples of the scaffold are formed using molds having parts that are formed of at least two materials having different thermal conductivities. The different conductivities enable a predetermined temperature gradient to be formed during fabrication of the scaffolds, which leads to directional phase separation and the formation of a controlled gradient of microtubules. Non-limiting examples of molds 10, 10', 10" suitable for forming these examples of the tubular scaffolds are shown in FIGS. 1A through 1C. Each of these molds 10, 10', 10" is a cylinder having a wall 12, a removable top 14, a removable bottom 16, and an insertable shaft 18 whose shape mimics that of the wall 12 but whose outer diameter is smaller than the inner diameter of the wall 12. In some instances, the removable bottom 16 and the insertable shaft 18 are a single piece (i.e., they are integrally formed as one piece).

In other examples, the insertable shaft 18 does not mimic the shape of the wall 12. The shaft 18 is the part of the mold 10, 10', 10" that determines the shape of the inner wall (see, e.g., $I_S$ in FIGS. 3 and 4) of the resulting scaffold (e.g., 20, 20', 20"), and thus may be any shape that corresponds with the desired shape for the scaffolds' inner wall. As such, in some examples, the insertable shaft 18 and the wall 12 have different shapes. For example, the wall 12 may have a circular cross-section while the insertable shaft 18 has a square cross-section. In these examples, the outer diameter of the insertable shaft 18 is still smaller than the inner diameter of the wall 12.

The wall 12 has an inner surface 13, and the shaft 18 has an outer surface 15. When the molds 10, 10', 10" are cylinders, both the inner surface 13 and the outer surface 15 have a diameter. In one example, the diameter of the outer surface 15 is about 3 mm, and the diameter of the inner surface 13 is about 5 mm. However, it is to be understood that the inner and outer surface 13, 15 diameters may be any desirable values, as long as the diameter of the outer surface 15 of the shaft 18 is smaller than the diameter of the inner surface 13 of the wall 12. The respective diameters may vary depending, at least in part upon the desired end use of the scaffold to be made using the mold(s) 10, 10', 10". Such diameters may also vary depending, at least in part, upon the desirable dimensions of the scaffold to be made using the mold(s) 10, 10', 10". In particular, the outer surface $O_S$ of the resulting scaffold corresponds to (i.e., takes on the general shape of) the inner surface 13 of the wall 12 (see FIGS. 3 and 4), and the inner surface $I_S$ of the resulting scaffold corresponds to (i.e., takes on the general shape of) the outer surface 15 of the shaft 18 (see also FIGS. 3 and 4).

When the molds 10, 10', 10" have a shape other than a cylinder, the dimensions of the mold may be different and the inner and outer surfaces 13, 15 may not have a diameter. For example, if the mold 10, 10', 10" is a cube, the wall inner surface 13 has 4 equal sides and the shaft outer surface 15 has 4 equal sides. The length of the sides that make up the inner surface 13 will be larger than the length of the sides that make up the outer surface 15. It is contemplated that other mold shapes and dimensions may be utilized, as long as the shaft 18 can be inserted into the wall 12. While other shapes may be used, it is believed that the cylindrical shape may be particularly desirable when creating blood vessel scaffolds. The removable top and bottom 14, 16 may be attached to the wall 12 via any suitable fastening means. For example, the top and bottom 14, 16 may be designed to be pushed into the respective top and bottom portions of the wall 12 or screwed into the respective top and bottom portions of the wall 12.

At least one of the parts 12, 14, 16, 18 of the mold 10, 10', 10" is formed of a material having a different thermal conductivity than the material used to form each of the other parts 12, 14, 16, 18. The two materials are a highly conductive material (e.g., metals, metal alloys (e.g., steel), etc.) and a minimally/low or non-conductive material. Examples of highly conductive materials include stainless steel, titanium and alloys thereof, aluminum, copper, silver, gold and alloys thereof. Examples of minimally conductive or non-conductive materials include polymers (e.g., nylons, polyesters, polyethylene, polypropylene, polytetrafluoroethylene, polystyrene, etc.), glasses, ceramics, porcelains, clays, and waxes.

It is to be understood that the high and low conductivity materials are selected relative to each other, and thus the actual conductivity values for "high" and "low" may vary depending upon the materials that are selected. In one example, the two materials are steel and polytetrafluoroethylene (PTFE). It is to be understood however, that any other materials having different thermal conductivities may be used.

The example shown in FIG. 1A has a high thermal conductivity material removable bottom 16, a low thermal conductivity material removable top 14, a low thermal conductivity material wall 12, and a low thermal conductivity material insertable shaft 18. The predetermined temperature gradient formed with this example of the mold 10 is formed in an axial direction where a warmer portion of the temperature gradient is adjacent the removable top 14 and a colder portion of the temperature gradient is adjacent the removable bottom 16. It is to be understood that this mold 10 could have a low thermal conductivity material removable bottom 16, a high thermal conductivity material removable top 14, a high thermal conductivity material wall 12, and a high thermal conductivity material insertable shaft 18. The predetermined temperature gradient formed with this example of the mold 10 is formed in an axial direction where a colder portion of the temperature gradient is adjacent the removable top 14 and a warmer portion of the temperature gradient is adjacent the removable bottom 16.

The example shown in FIG. 1B has a high thermal conductivity material wall 12, a low thermal conductivity material removable top 14, a low thermal conductivity material removable bottom 16, and a low thermal conductivity material insertable shaft 18. The predetermined temperature gradient formed with this example of the mold 10' is formed in a radial direction where a colder portion of the temperature gradient is adjacent the wall 12 and a warmer portion of the temperature gradient is adjacent the insertable shaft 18.

The example shown in FIG. 1C has a low thermal conductivity material wall 12, a high thermal conductivity material removable top 14, a high thermal conductivity material removable bottom 16, and a high thermal conductivity material insertable shaft 18. The predetermined temperature gradient formed with this example of the mold 10" is formed in a radial direction where a colder portion of the temperature gradient is adjacent the insertable shaft 18 and a warmer portion of the temperature gradient is adjacent the wall 12.

When forming the scaffolds using the mold(s) 10, 10', 10", a polymer solution containing a polymer and a solvent is poured into the space formed between the wall 12 and the insertable shaft 18 of any of the molds 10, 10', 10". The polymer solution may include biodegradable polymers suitable for tissue regeneration. Some examples of biodegradable polymers include poly(L-lactic acid) (PLLA), polyglycolic acid (PGA), poly(lactide-co-glycolide) (PLGA), and/or mixtures thereof. Some other suitable biodegradable polymers include at least one of poly(D,L-lactic acid) (PDLLA), polyanhydrides, poly(ortho ethers), poly(ε-caprolactone) (PCL), poly(hydroxy butyrate) (PHB), poly(propylene fumarate) (PPF), polyphosphoesters (PPE), polyphosphazenes, and mixtures thereof. Further suitable examples include degradable natural macromolecules (typically enzymatically degradable) such as collagen, gelatin, and many other proteins, carbohydrates, and their derivatives. Some examples of water-soluble (hydrophilic) polymers/macromolecules that are suitable for the polymer solution include polyvinyl alcohol, polyethylene oxide (polyethylene glycol), polymethacrylic acid (PMAA), polyvinyl pyrolidone, polyacrylic acid, poly(lysine), poly(allylamine), poly(ethylenimine), poly(acrylamide), poly(acrylamide-co-acrylic acid), poly(acrylamide-co-diallyldimethylammonium chloride), poly(vinyl alcohol), poly(ethylene glycol), polyethylene-block-poly(ethylene glycol), poly(propylene glycol), poly(2-hydroxypropyl methacrylate), poly(2-hydroxyethyl methyacrylate), poly(4-hydroxystyrene), polyethylene monoalcohol, poly(vinyl alcohol-co-ethylene), poly(styrene-co-allyl alcohol), hydroxyethylcellulose, alginate, pectin, chitin, chitosan, dextran, hyaluronic acid, collagen, gelatin, and mixtures thereof.

The polymer is dissolved in a suitable solvent so that the polymer concentration ranges from about 2 wt % to about 10 wt %. Examples of suitable solvents include tetrahydrofuran (THF), benzene, mixtures of benzene and THF, mixtures of water and methanol, mixtures of THF and methanol, mixtures of dioxane and methanol, and mixtures of dioxane and water.

After the polymer solution is poured into the mold 10, 10', 10", the mold 10, 10', 10" and polymer solution are exposed to a temperature ranging from −200° C. to room temperature (e.g., about 20° C.). The lower temperatures within this range may be achieved using liquid nitrogen. This forms the temperature gradient in the mold 10, 10', 10" and thermally induces phase separation of the polymer solution into a polymer/solvent system. The phase separated polymer/solvent system is removed from the mold 10, 10', 10" and is freeze-dried. The polymer/solvent system gels (i.e., becomes an elastic solid-like material) as a result of phase separation and thus it can easily be taken out of the mold 10, 10', 10" once the top 14 or bottom 16 is removed. Freeze-drying may be accomplished at a temperature less than 0° C. Temperatures may be as low as, in some instances, −200° C. In one example, freeze-drying is accomplished at a temperature ranging from about −5° C. to about −10° C. in an ice/salt bath under vacuum. In another example, freeze-drying is accomplished in the presence of a car coolant. This process results in the scaffold having a solid-wall polymeric structure and a controlled gradient of microtubules oriented axially or radially therein, depending upon the mold 10, 10', 10" used. By "solid-wall" it is meant that the polymer walls of the scaffold do not include any fibers.

Figure 2:
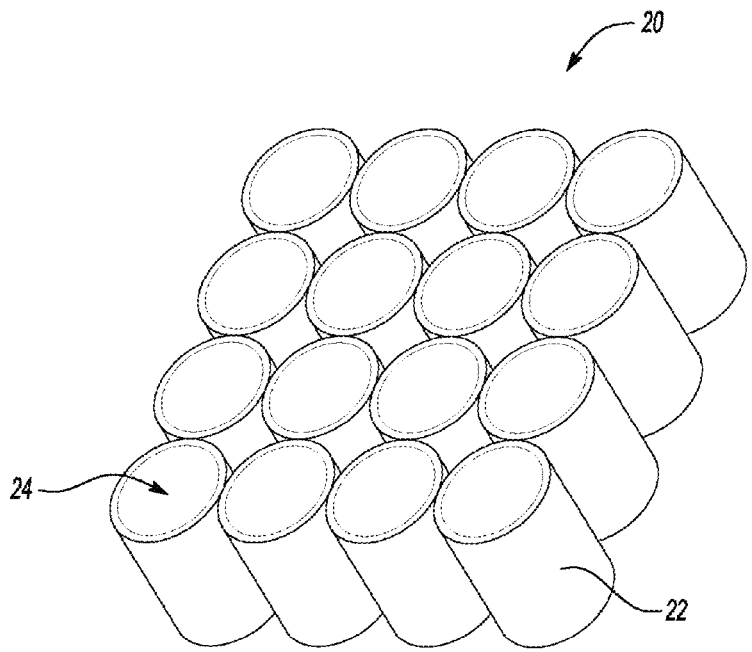
FIG. 2 is a schematic perspective view of an example of a microtubule structure of a scaffold formed with an axial temperature gradient.

FIG. 2 illustrates a schematic perspective view of the scaffold 20 including the solid-wall microtubules 22 and the microtubule pores 24 formed using the mold 10 of FIG. 1A. The mold 10 having a high thermal conductivity material bottom 16 and low thermal conductivity material wall 12, shaft 18, and top 14 results in a temperature gradient formed from the bottom 16 (lower temperatures) to the top 14 (higher temperatures). This gradient is maintained uniaxially during the thermally induced phase separation process. Using the mold 10 and the method described above, the characteristic architecture of an array of parallel microtubules 24 is achieved (see the schematic depiction in FIG. 2). In this example when the polymer solution includes benzene as the solvent of poly(L-lactic acid), the cross-sections of the resulting microtubules 22 are polygons with 3 to 7 sides. The porosity of the scaffold 20 formed using the mold 10 ranges from 70% to 99% of the total volume, where a higher concentration of the polymer in the polymer solution results in a reduced porosity of the scaffold 20. In one example, the concentration of the polymer ranges from about 1% to about 10% and the porosity ranges from 90% to 99%. The average microtubule pore 24 size (e.g., length and/or width) ranges from about 20 μm to about 500 μm, where a higher concentration of polymer in the polymer solution results in a reduced microtubule pore size. In one example, the average microtubule pore size ranges from about 50 μm to about 200 μm. It is believed that the phase separation temperature used in the method also affects the microtubule pore 24 size. The lower the phase separation temperature, the greater the reduction in pore size (see, e.g., Table 1 in Example 1).

In one example using the mold 10, the desirable polymer concentration in the polymer solution is 2.5 wt %, the resulting scaffold 20 has porosity of about 95%, and the average microtubule pore size of the resulting scaffold 20 ranges from about 120 μm to about 150 μm.

Figure 3:
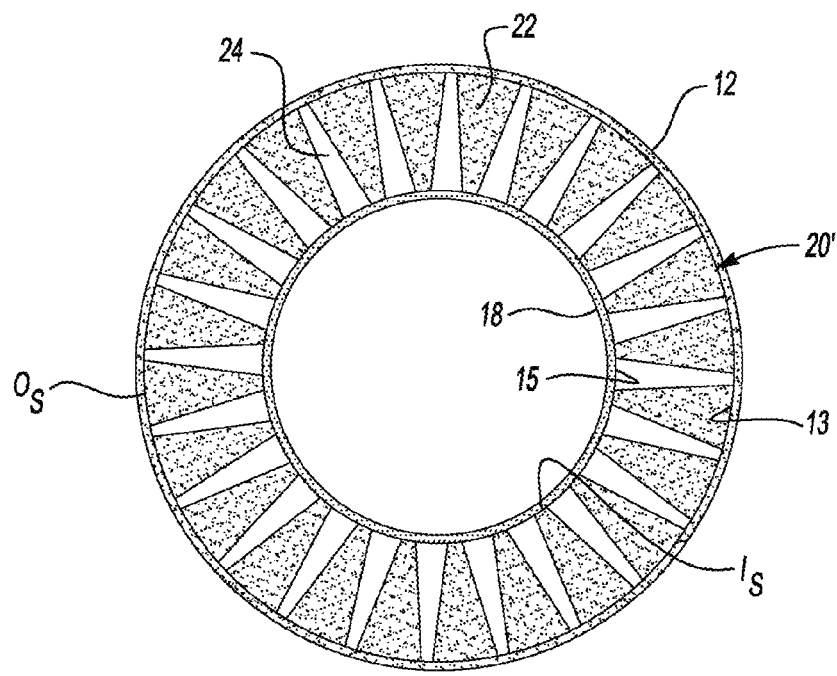
FIG. 3 is a schematic top view of an example of a microtubule structure of a scaffold formed with a radial temperature gradient.

FIG. 3 illustrates a schematic top view of the vessel scaffold 20' including the solid-wall microtubules 22 and microtubule pores 24 formed using the mold 10' of FIG. 1B. The wall 12 and shaft 18 of the mold 10' are shown in FIG. 3. The mold 10', having a high thermal conductivity material wall 12 and a low thermal conductivity material bottom 16, shaft 18, and top 14, results in a temperature gradient formed in the radial direction from the wall 12 (lower temperatures) to the shaft 18 (higher temperatures). The microtubule pores 24 formed in this example decreased in size gradually from the inner wall $I_S$ of the scaffold 20' to the outer wall $O_S$ of the scaffold 20'.

Figure 4:
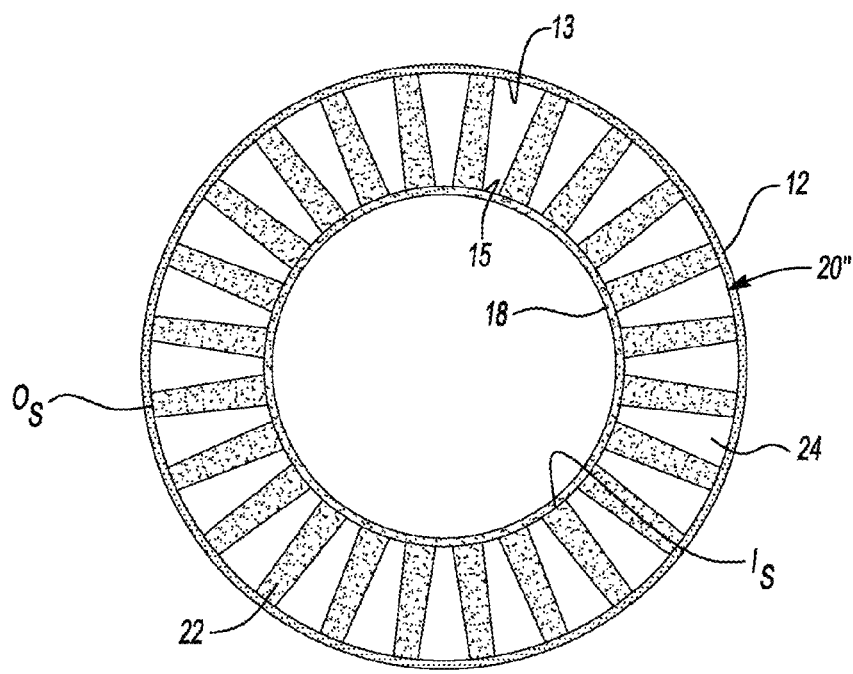
FIG. 4 is a schematic top view of another example of a microtubule structure of a scaffold formed with a radial temperature gradient.
Figure 6A:
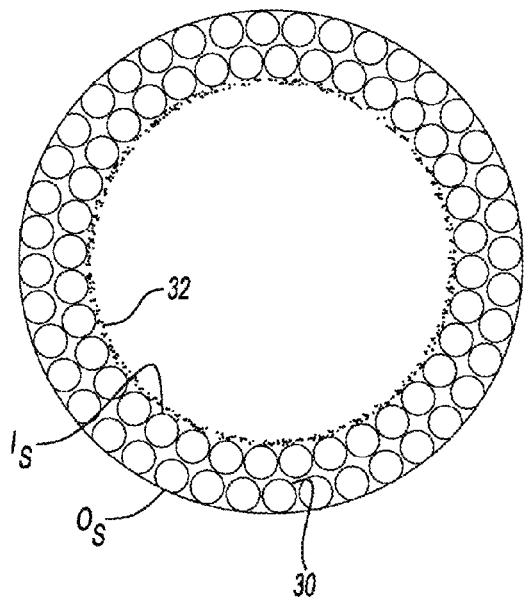
FIGS. 6A through 6D are schematic top views of examples of multilayered scaffolds.
Figure 6B:
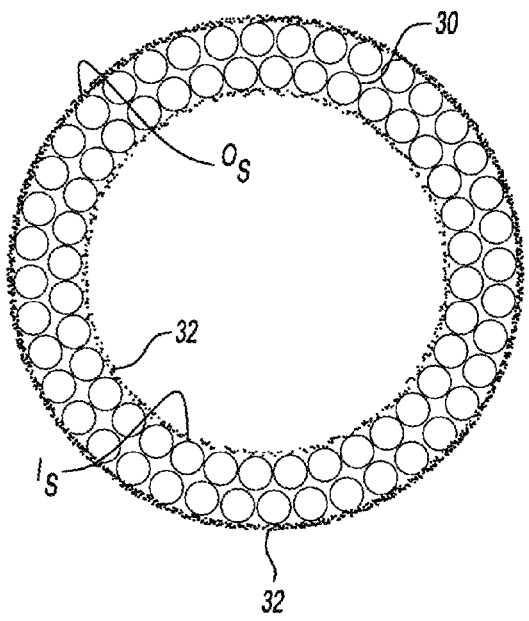
Figure 6C:
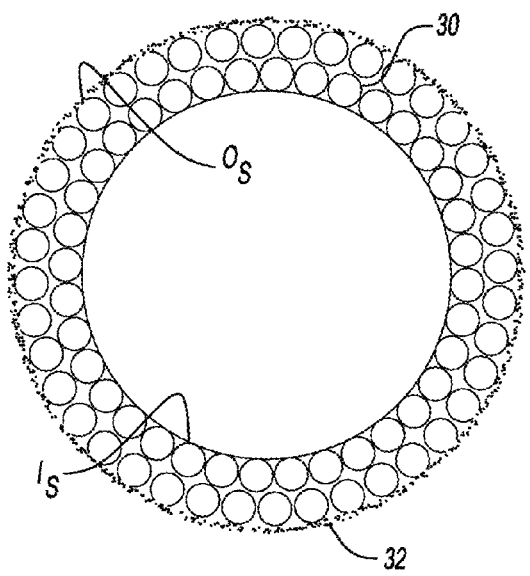
Figure 6D:
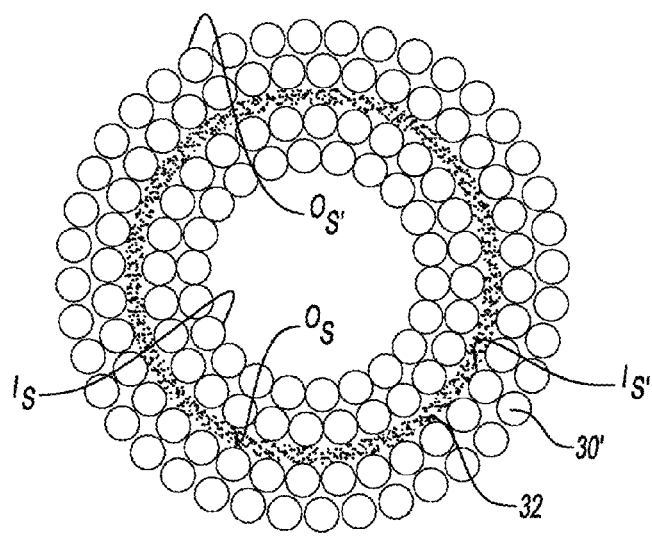

FIG. 4 illustrates a schematic top view of the vessel scaffold 20" including the solid-wall microtubules 22 and microtubule pores 24 formed using the mold 10" of FIG. 1C. The wall 12 and shaft 18 of the mold 10" are shown in FIG. 4. The mold 10", having a low thermal conductivity material wall 12 and a high thermal conductivity material bottom 16, shaft 18, and top 14, results in a temperature gradient formed in the radial direction from the wall 12 (higher temperatures) to the shaft 18 (lower temperatures). The microtubule pores 24 formed in this example decreased in size gradually from the outer wall $O_S$ of the scaffold 20" to the inner wall $I_S$ of the scaffold 20".

As illustrated in FIGS. 3 and 4, the scaffolds 20' and 20" are oriented in fishbone-like architectures, which have parallel microtube pores 24 with thin partitions therebetween. The microtube pore 24 diameters become radially larger or smaller along the direction of the temperature gradient (discussed further in Example 1), and the size of the microtubule pores 24 is also reduced with an increasing polymer concentration (again, see Table 1 in Example 1). While the radial temperature gradient direction does not significantly affect the average microtubule pore 24 size at the same polymer concentration, the microtubule pore 24 size formed under the radial temperature gradient is reduced (e.g., from 200 μm to 20 μm) when the temperature decreases (e.g., from −20° C. to −196° C.).

In any of the examples of the scaffold 20, 20', 20" formed using the mold 10, 10', 10", at least one of a size of the microtubule pores 24, a porosity of the vessel scaffold 20, 20', 20", or an orientation of the microtubule pores 24 may be controlled by i) altering the concentration of polymer in the polymer solution, ii) altering the temperature, and/or iii) altering the at least two materials of the parts of the mold 10, 10', 10".

In another example, the scaffold formed is a tubular nano-fibrous wall polymer structure in which the polymer walls include a plurality of nano-fibers (i.e., string-like pieces, each of which has a diameter on the nano-scale (from about 1 nm to about 1000 nm). The nano-fibers form a substantially continuous fibrous network. The average length between two junctions ranges from about 500 nm to about 5000 nm, or from about 1000 nm to about 3000 nm. The tubular scaffold is porous, and thus includes an oriented and interconnected microtubular porous network.

Forming the nano-fibrous scaffold involves either a one-step phase separation, or a two-step phase separation including a solid-liquid phase separation and then a liquid-liquid phase separation (e.g., when a solvent mixture system of benzene/THF is used).

The formation of nano-fibers using the one-step phase separation process depends, at least in part, upon the polymer type, polymer concentration, solvent or solvent mixture, and phase separation temperature that are selected. With this method, the nano-fiber formation is believed to result from a suitable liquid-liquid phase separation followed by crystallization to stabilize the nano-fiber structure.

The two step phase separation process is schematically illustrated in FIGS. 5A through 5C. As illustrated in FIG. 5A, a homogeneous polymer solution is prepared using one or more of the previously listed polymers (present in a total amount ranging from 1 wt % to 20 wt %, or in another example from 2.5 wt % to 10 wt %) and at least one solvent that dissolves the selected polymer(s) (i.e., any of the previously listed solvent(s)). In one non-limiting example, the solvent is a solvent mixture including a predetermined ratio of benzene to tetrahydrofuran ranging from 8:2 (v/v) to 6:4 (v/v).

The polymer solution is poured into a tubular shaped mold including a cylindrical wall, a removable top, a removable bottom, and an insertable shaft whose shape mimics that of the wall but whose outer diameter is smaller than the inner diameter of the wall. In some instances, the removable bottom and the insertable shaft are a single piece. In this embodiment, the mold may be formed of a single material (e.g., metal, glass, ceramic, polymer) or may be the molds described herein above in reference to FIGS. 1A through 1C, which will induce a temperature gradient during the solid-liquid phase separation to achieve radial or axial microtubules in the final nano-fibrous wall polymer structure.

As shown in FIG. 5B, the solid-liquid phase separation is induced by exposing the mold and the polymer solution therein to a temperature ranging from −200° C. to 20° C., thereby forming a solidified solvent phase and a polymer-rich phase. In the example of the benzene/THF solvent mixture, benzene has a much higher freezing temperature than THF. Therefore, during the first stage of the solid-liquid phase separation, the crystallization of benzene creates micropores/microtubules.

As shown in FIG. 5C, the liquid-liquid phase separation is induced by immersing the mold, the solidified solvent phase, and the polymer-rich phase into a bath of hexane for a predetermined time, thereby extracting the at least one solvent and forming a polymer scaffold. The hexane may be changed multiple times during this predetermined time period. It is to be understood that solvents other than hexane may be used in order to accelerate removal of the remaining solvent. After the predetermined time period expires, cyclohexane (or another solvent that can exchange with the solvent and can be easily sublimated) is exchanged for the hexane. The polymer scaffolds are removed from the cyclohexane and from the mold, and are frozen. It is believed that the liquid-liquid phase separation and the decreasing temperature induces and enhances nano-fiber formation in the polymer scaffold. It is believed that the nano-fibrous structure is formed during the second stage by spinodal liquid-liquid phase separation and subsequent crystallization of the polymer-rich phase.

Examples of the method described to form the nano-fibrous wall tubular scaffold may be performed in the absence of a porogen material (e.g., when the benzene/THF solvent mixture is used) or in the presence of a porogen material (e.g., when single solvents are used (e.g., benzene, THF, etc.)). When a porogen material is used (e.g., sugar spheres), it is to be understood that the porogen material is added to the mold prior to introducing the polymer solution into the mold. The porogen material is leached out after the freezing of the polymer scaffold.

In still another embodiment, the scaffold is a composite scaffold including at least two different types of scaffolds. These composite scaffolds may be formed in any desirable shape, including flat films, three-dimensional scaffolds, or tubular scaffolds.

Examples of composite scaffolds are shown in FIGS. 6A through 6D, and each includes at least one porous polymeric structure 30, 30' having an inner surface $I_S$, $I_{S'}$ and an outer surface $O_S$, $O_{S'}$. At least one electrospun layer 32 is positioned along at least one of the inner surface $I_S$, $I_{S'}$ (see FIG. 6A), or the outer surface $O_S$, $O_{S'}$ (see FIG. 6C), or both the inner and outer surfaces $I_S$, $I_{S'}$, $O_S$, $O_{S'}$, (see FIG. 6B), or in the middle of the composite or between two scaffolds (see FIG. 6D). While not shown, it is to be understood that the porous polymeric structure 30, 30' may be a solid-wall porous polymeric structure, or a nano-fibrous wall porous polymeric structure. Sill further, various combinations of solid-wall and nano-fibrous wall porous polymeric structures may be used in the composite scaffolds.

The electrospun scaffolds are formed by preparing a polymer solution and then electrospinning the solution, for example, onto a rotating collector. One example of a suitable polymer solution is prepared by dissolving poly(ε-caprolactone) (PCL) in dichloromethane/acetone (2:1 volume ratio) at a concentration of 12.5%. It is contemplated that other polymers and/or solvents may be used in this process. For example, other suitable solvents include chloroform, THF, acetone, ethyl acetate, and mixtures thereof. One example of an electrospinning apparatus 40 is shown in FIG. 7. A suitable voltage (e.g., 15 kV) is applied by a voltage regulated DC power supply 42 to generate the polymer jet. The resulting PCL fibers are collected on a rotating collector 44 with a constant rotating speed to form a scaffold.

The examples of the methods disclosed herein may be used to form the solid-wall porous polymeric structure or the nano-fibrous wall porous polymeric structure. It is to be understood that either the single step solid-liquid phase process or the two-step (solid-liquid and then liquid-liquid) phase separation process may also be used to form the nano-fibrous wall porous polymeric structure. It is to be further understood that the temperature gradient method disclosed herein may also be used to form the solid-wall porous polymeric structure or the nano-fibrous wall porous polymeric structure.

In one example, a mold (such as those described herein) including top and bottom plates, an inner shaft, and an outer cylinder (all made of PTFE) is used to form the scaffolds. In this example, the mold may have any desirable diameters, and one embodiment has an inner-diameter (i.e., shaft diameter) of 2 mm and an outer-diameter (i.e., wall diameter) of 3 mm. This mold does not create a gradient as described above. For solid-wall porous scaffolds, dioxane is used as the solvent for PLLA. For nano-fibrous wall porous scaffolds, THF is used as the solvent for PLLA. A sugar template may be introduced into the mold during the phase separation and then is leached out to create the highly porous and interconnected pore structure.

The electrospun layer 32 and scaffold(s) 30, 30' may then be layered in a desirable manner. When the electrospun layer 32 is formed on an outer wall $O_S$, the phase-separated scaffold 30 is produced and then the layer 32 is electrospun on the outer layer $O_S$ of the scaffold(s) 30, 30' as shown in the device illustration of FIG. 7. When the electrospun layer 32 is formed on an inner wall $I_S$ or as a middle layer, the electrospun tube is formed first and then is assembled into the mold before casting the porogen materials (when used) and polymer solution therein.

In still another example, the different layers of a multilayered scaffold have different pore sizes with or without the electrospun fibrous layer 32.

Figure 32:
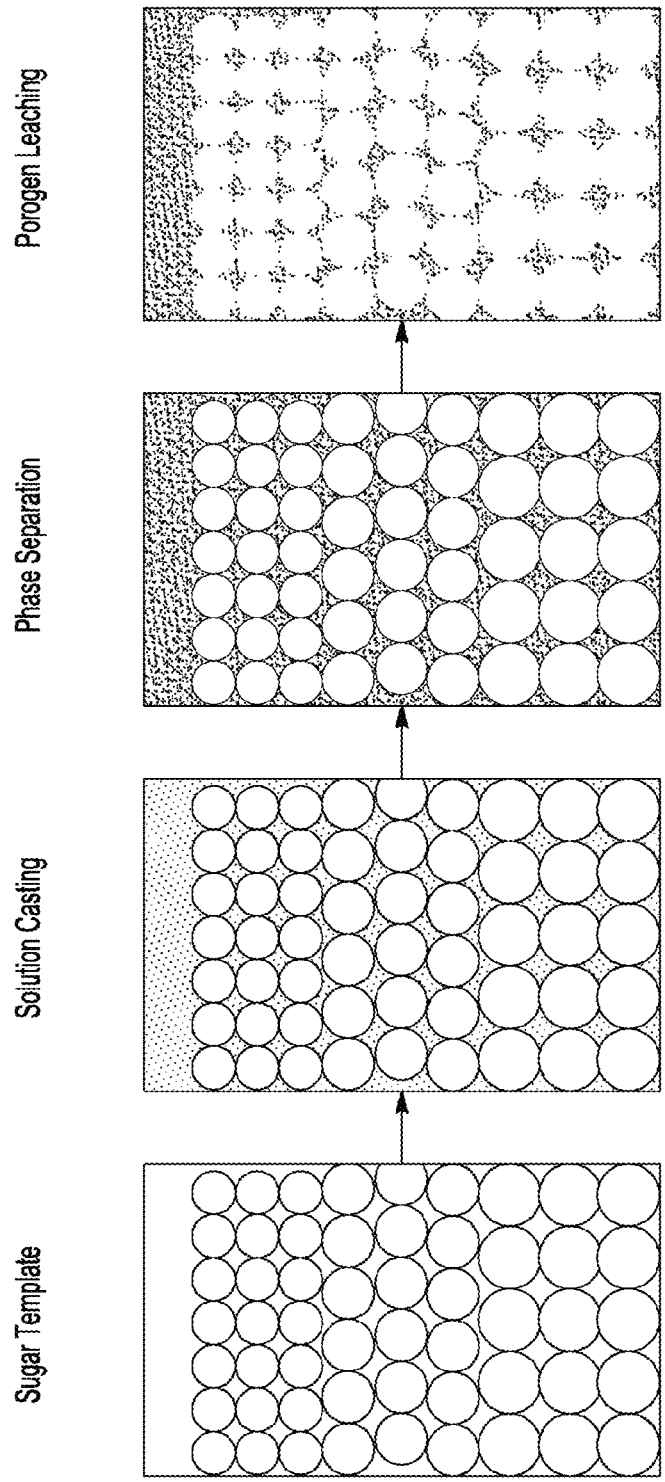
FIG. 32 is a schematic diagram illustrating the preparation of graded pore structure scaffolds using graded sugar templates.

Other examples of the scaffolds disclosed herein include scaffolds with graded pore structures that are formed using a graded porogen template. This process is shown schematically in FIG. 32. As illustrated in the first box of FIG. 32, a sugar template (or other porogen material template) includes sugar spheres of different sizes that are oriented in a mold according to their size. As such, the sugar template provides a gradient of differently sized sugar spheres and differently sized pores between the sugar spheres. Sugar spheres of different sizes are prepared by an emulsion technique. For example, a suitable sugar (e.g., d-fructose) is melted and emulsified into an oil with a predetermined amount of surfactant (which changes depending upon the system used) at a temperature at or above the melting temperature of the sugar (e.g., about 120° C.) under stirring. The order of the addition of the porogens (e.g., smaller sized porogens in the lower layers and larger sized porogens in the upper layers) or the sizes of the porogens are selected so that the smaller porogens do not penetrate into the interstitial spaces of the larger porogens and/or so that the smaller porogens are purposely arranged into multi-sized pore structures with their penetration into the interstitial spaces of the larger porogens. The resulting mixture is cooled down to solidify the sugar spheres. After discarding the oil, the sugar spheres are washed with a suitable non-solvent (e.g., hexane) and are sieved to select desired sizes (groups of which may range from 125 μm to 250 μm, and from 250 μm to 425 μm, and from 425 μm to 600 μm). The sieved sugar spheres are packed sequentially according to the sugar sphere size (e.g., larger to smaller, or smaller to larger) in a mold (e.g., a single material tubular mold as previously described) with a non-solvent (e.g., hexane) and are heat treated for a certain time period to form the sugar sphere template. Heating bonds the sugar spheres, and then the non-solvent may be removed. The resulting sugar template may be dried under vacuum.

To form the scaffold in this example, a polymer solution (such as those previously described) is cast into the mold containing the assembled sugar template. If desirable, a mild vacuum may be applied to fully fill the interspaces between adjacent spheres of the sugar template (see, e.g., the second box of FIG. 32). Phase separation is then induced by exposing the polymer solution/sugar template to a temperature ranging from −200° C. to 20° C. for a predetermined time period. The phase separated polymer solution/sugar template then undergoes a solvent exchange process to remove the solvent of the polymer solution. The resulting composites are freeze-dried, and the sugar template leached away (e.g., using a suitable solvent of the sugar template). The highly porous nano-fibrous scaffold (with a graded pore structure) may be again freeze-dried.

It is to be understood that any of the examples disclosed herein may be combined together. For example, the multi-material molds may be used with the solvent mixture, or either or both of these techniques may be combined with the varying-sized porogen template. In one specific example, the techniques are combined (i.e., the multi-material mold is combined with the varying-sized porogen) so that a second level of graded pores or/and oriented tubular pores would be formed in the pore walls surrounding the sugar spheres. In this example, the thickness of the individual sections of the graded scaffold can be controlled in the preparation of the scaffold by adding different amounts of sugar spheres with different sizes. By varying the sugar sphere size, one can also achieve different macropore sizes. Furthermore, the size of the sugar sphere is easy to control in the whole micrometer ranges by adjusting the amount of surfactant. Therefore, different graded templates with varying structures can be created as required and/or desired. As such, this example of the methods disclosed herein may be used to engineer a final graded macro- and micro-architecture including controlled porosity, macropore size, interpore opening size, and section thickness.

By combining the liquid-liquid phase separation method with the graded porogen template, a nano-fibrous wall structure can be generated in the scaffold along with the graded pore structure.

To illustrate the present disclosure, the following examples are provided. However, these examples are intended to be illustrative and should not be considered to limit the scope of the present disclosure.

General Information for Examples 1 and 2

Materials

PLLA with an inherent viscosity of 1.4-1.8 dl/g was purchased from Boehringer Ingelheim (Ingelheim, Germany) and was used as received. Benzene, THF and other reagents were obtained from Aldrich Chemical Company (Milwaukee, Wis.). They were of analytical grade and used without further treatment.

Structure/Property Characterization

To estimate the density and porosity of the PLLA scaffolds formed in Examples 1 and 2, the inner-diameter, outer-diameter and height of each scaffold were measured after freeze-drying to calculate the volume of each scaffold. The mass of each scaffold was measured with an analytical balance, and the overall density $D_f$ was calculated from the volume and the mass. The porosity $\varepsilon$ of each scaffold was calculated from the measured overall density $D_f$ of the fibrous matrix and the skeletal density $D_p$ using previously described techniques. Porosity was defined as:

$$\varepsilon = \frac{D_p - D_f}{D_p}$$

and the skeletal density $D_p$ of the scaffolds was given by:

$$D_p = \frac{1}{\frac{1 - X_c}{D_a} + \frac{X_c}{D_c}}$$

where $X_c$ was the degree of crystallinity determined with differential scanning calorimetry. For PLLA, $D_a$=1.248 g/mL (density of amorphous polymer) and $D_c$=1.290 g/mL (density of 100% crystalline polymer).

Porous morphologies of the scaffolds formed in Examples 1 and 2 were examined using scanning electron microscopy (SEM) (S-3200N, Hitachi, Japan). To expose the internal architecture, samples were cut carefully with a razor blade after freeze-drying. All samples were coated with gold using a sputter coater (Desk-II, Denton Vacuum Inc., Moorstown, N.J.), where the pressure was below 50 mTorr, the current was approximately 40 mA, and the coating time was 120 seconds. The diameters of the pores and the nano-fibers (in Example 2) were measured from SEM micrographs using Image-pro plus software (Media Cybernetics). More than 40 micropores and nano-fibers (in Example 2) were chosen to calculate an average diameter. To determine the gradient structure of the pores, each wall thickness was divided into ten equal parts from the inner-wall to the outer-wall or from outer-wall to inner-wall.

The compressive mechanical properties of the PLLA scaffolds formed in Examples 1 and 2 were measured with an MTS Synergie 200 mechanical tester (MTS Systems Corporation, Eden Prairie, Minn.). For compression testing, the specimens were homocentric tubes measuring 5 mm in outer-diameter, 3 mm in inner-diameter and 3.0 mm in height. The load was applied in the direction either parallel or perpendicular to the tubular axis. The crosshead speed was 0.5 mm/min and the compressive modulus was defined as the initial linear modulus. The yield strength was determined from the cross point of the two tangents on the stress-strain curve around the yield point. At least 5 specimens were tested for each sample.

Histological Analysis

Implants were washed in PBS, fixed with 3.7% formaldehyde in phosphate buffered saline (PBS) overnight, dehydrated through a graded series of ethanol, embedded in paraffin, and sectioned at a thickness of 5 µm. Sections were deparaffinized, rehydrated with a graded series of ethanol, and stained with hematoxylin and eosin (H-E).

Example 1

Vessel Scaffold Fabrication

Three different molds were designed to fabricate different blood vessel scaffolds with orientation and gradient pore structures. The molds were composed of a top plate, a bottom plate, an inner shaft, and an outer cylinder made of the same or different materials (see FIGS. 1A through 1C). In this example, each mold included parts made of steel and other parts made of PTFE (according to the embodiments described in FIGS. 1A through 1C), and was intended to create different temperature gradients. Each mold had an inner-diameter of 3.00 mm and an outer-diameter of 5.00 mm.

PLLA was dissolved in benzene to form homogeneous solutions with concentrations ranging from 2.5% to 10%. The polymer solutions were poured into different molds then transferred into a freezer set to a predetermined temperature to induce phase separation. The phase-separated polymer/solvent system was then transferred into a freeze drying vessel at a temperature ranging from $-5°$ C. to $-10°$ C. in an ice/salt bath, and was freeze-dried under vacuum (pressure lower than 0.5 mmHg) for 72 hours. The dried scaffolds were then kept in a desiccator until characterization or usage.

Radial Oriented Scaffold Structure

When the mold was composed of a steel wall and PTFE bottom/top/shaft, a temperature gradient was formed in the radial direction from the outside (colder) to the inside (warmer) (see FIG. 3). The radially oriented gradient pore structures of these PLLA scaffolds were microtubes whose size decreased gradually from inside wall to outside wall (referred to as I/O in the following discussion). The SEM micrographs of the cross-sections of the vessel scaffolds prepared using this mold are shown in FIGS. 9A through 9D.

When the mold was composed of a steel shaft/bottom/top and a PTFE wall, a temperature gradient was formed in the radial direction either from outside (warmer) to inside (colder) (see FIG. 4). The radially oriented gradient pore structures of these PLLA scaffolds were microtubes whose size gradually decreased from outside wall to inside wall (referred to as O/I in the following discussion). The SEM micrographs of the cross-sections of the vessel scaffolds prepared using this mold are shown in FIGS. 10A through 10D.

Figure 8:
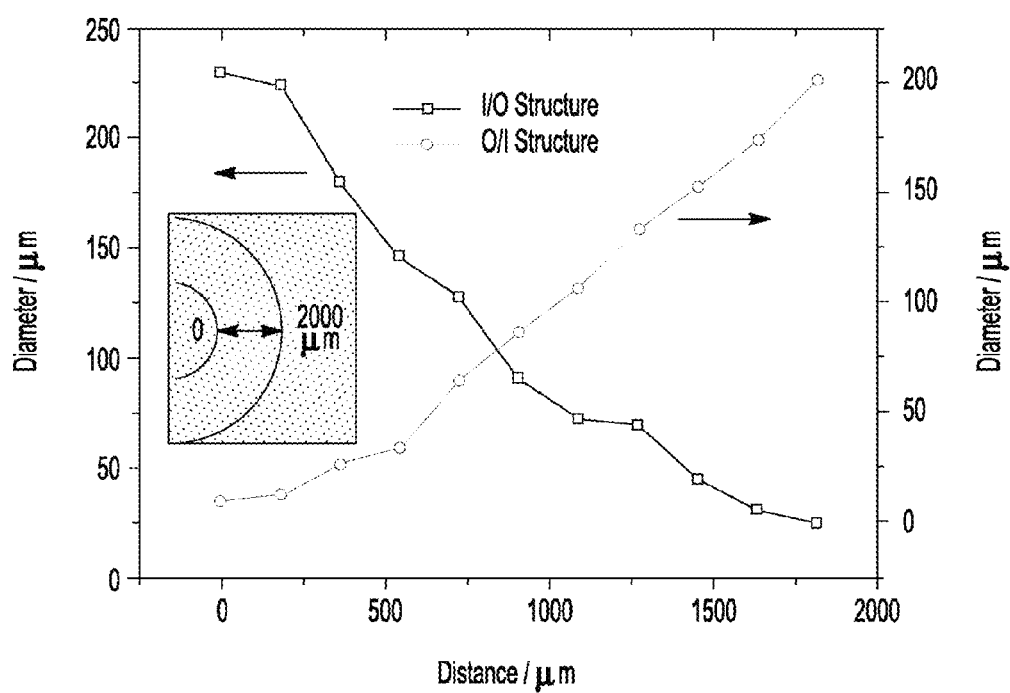
FIG. 8 is a graph illustrating the pore size of a radially oriented gradient microtubular structure formed from PLLA/benzene solutions with PLLA concentration of 5.0% and at a phase separation temperature of −20° C.
Figure 9A:
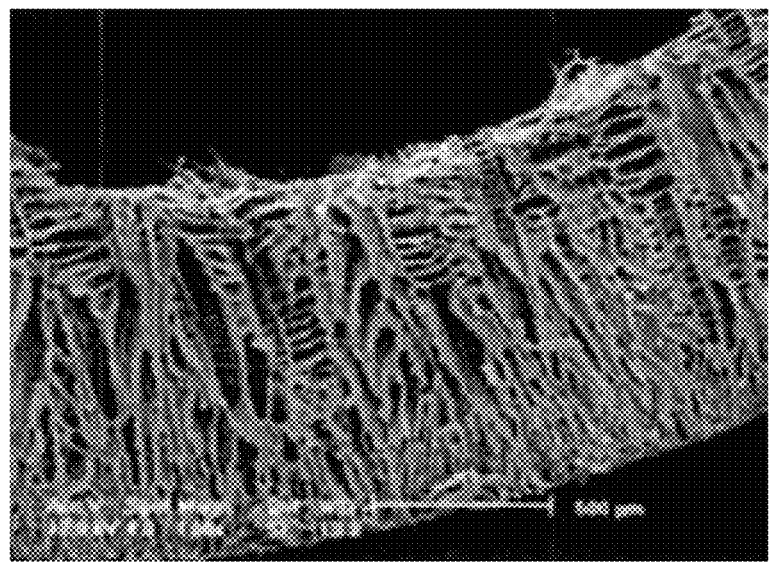
FIGS. 9A through 9D are scanning electron micrograph (SEM) images of cross sections of vessel scaffolds prepared under radial temperature gradient (I/O structure) at −20° C. for PLLA/benzene solutions with different concentrations (wt/v): (A) 2.5%; (B) 5.0%; (C) 7.5%; (D) 10.0%.
Figure 9B:
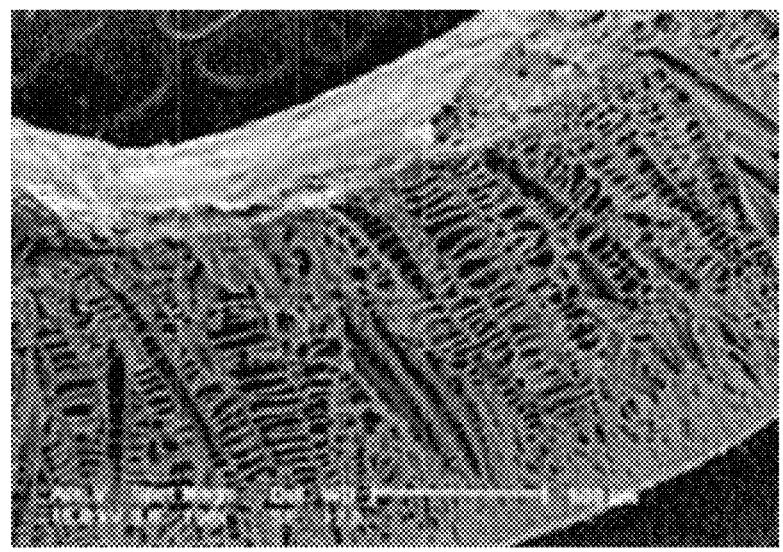
Figure 9C:
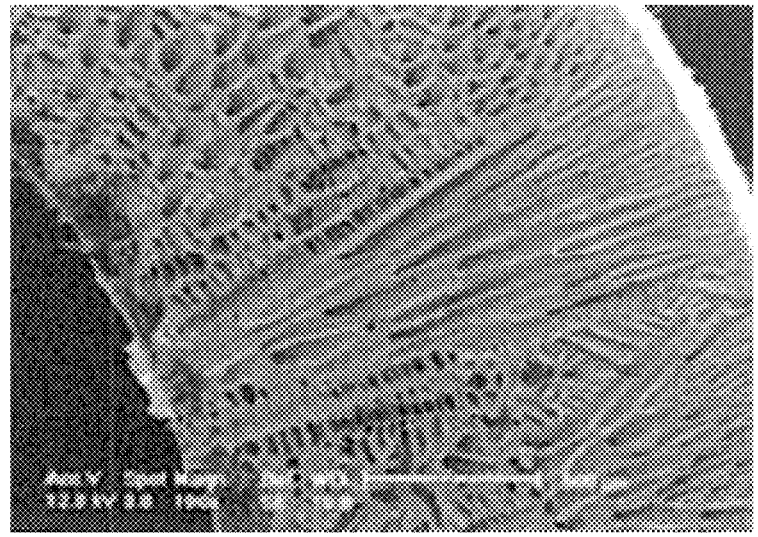
Figure 9D:
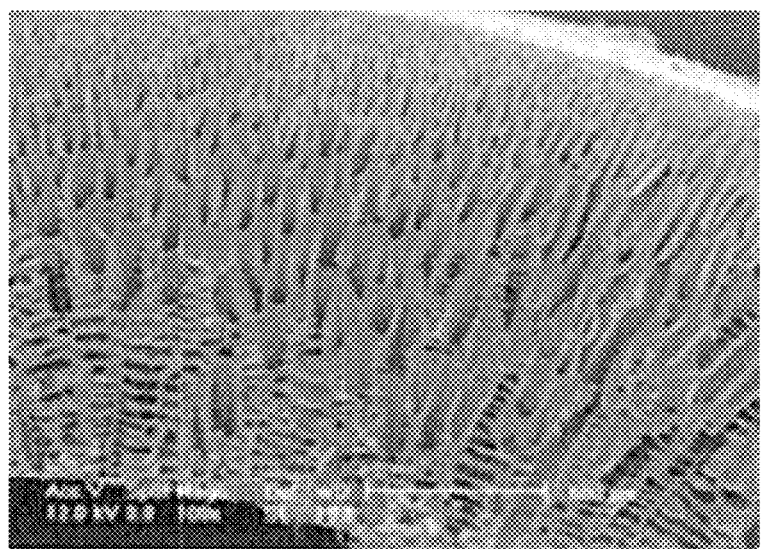
Figure 10A:
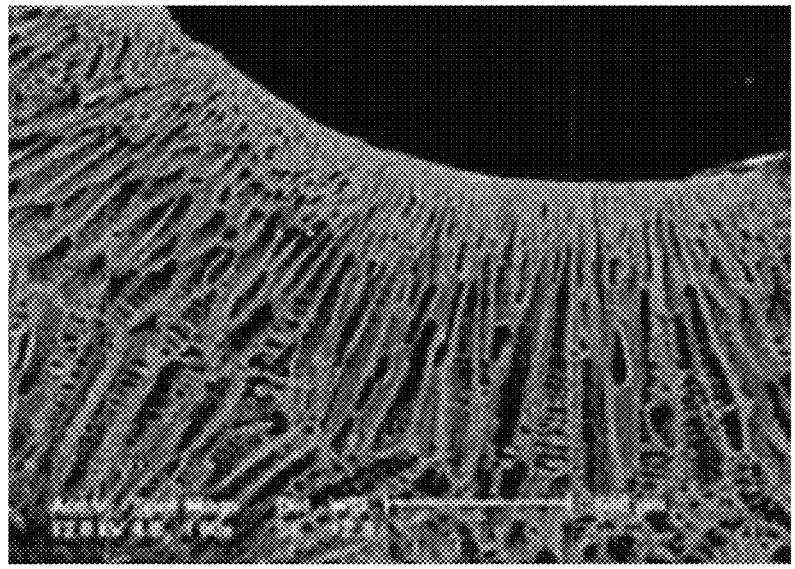
FIGS. 10A through 10D are SEM images of cross sections of vessel scaffolds prepared under radial temperature gradient (O/I structure) at −20° C. from PLLA/benzene solutions with different concentrations (wt/v): (A) 2.5%; (B) 5.0%; (C) 7.5%; (D) 10.0%.
Figure 10B:
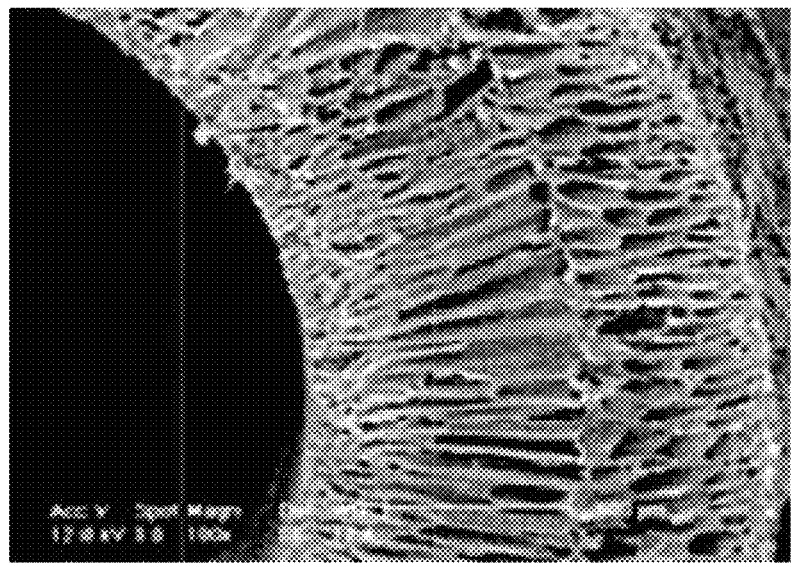
Figure 10C:
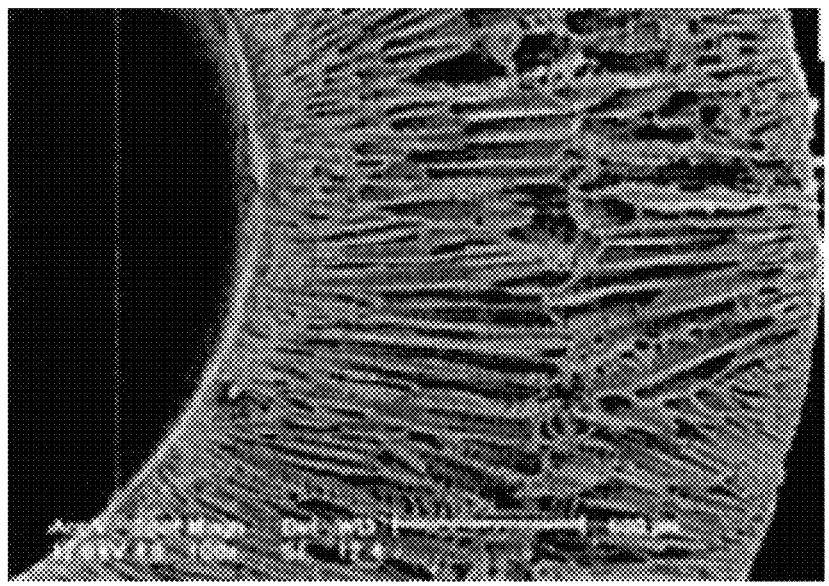
Figure 10D:
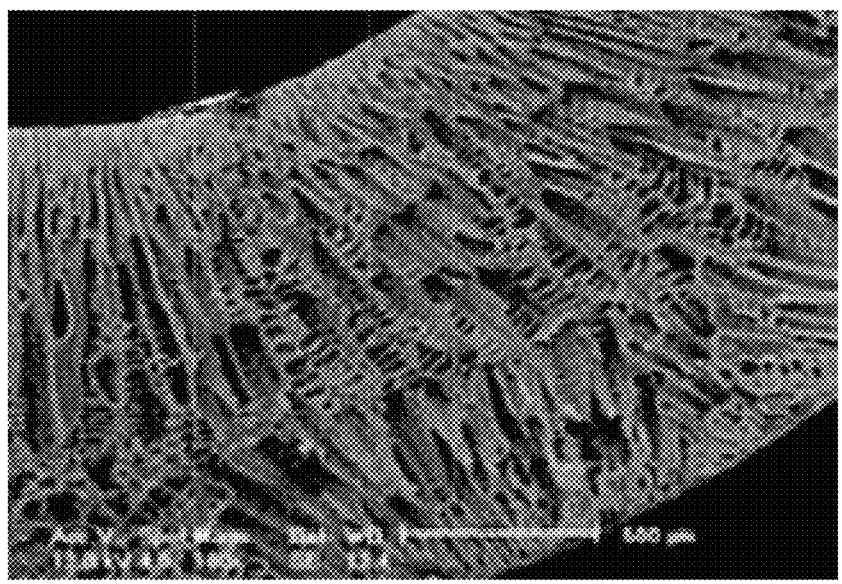
Figure 11A:
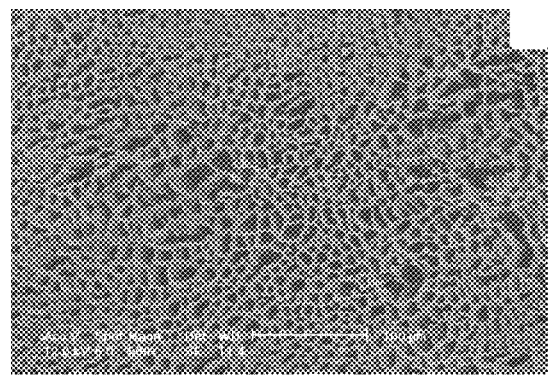
FIGS. 11A through 11C are SEM images of cross sections of vessel scaffolds prepared using 5.0% (wt/v) PLLA/Benzene solution at −196° C.: (A) axial, (B) O/I structure; (C) I/O structure.
Figure 11B:
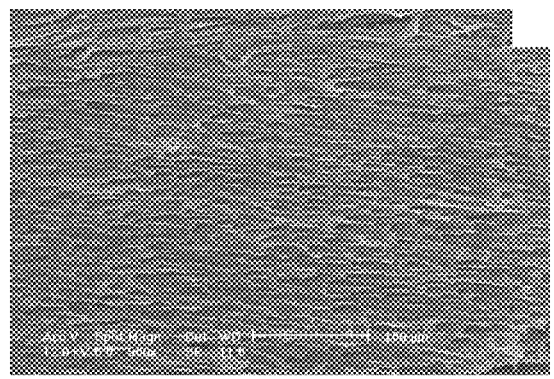
Figure 11C:
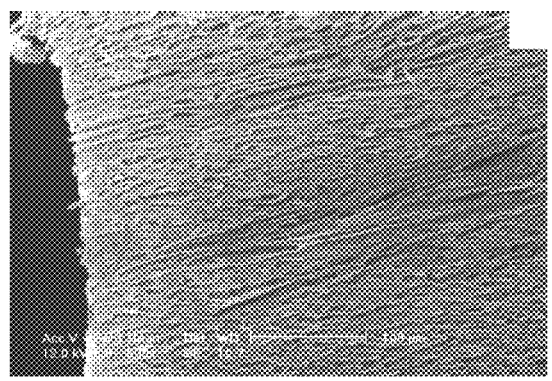
Figure 12A:
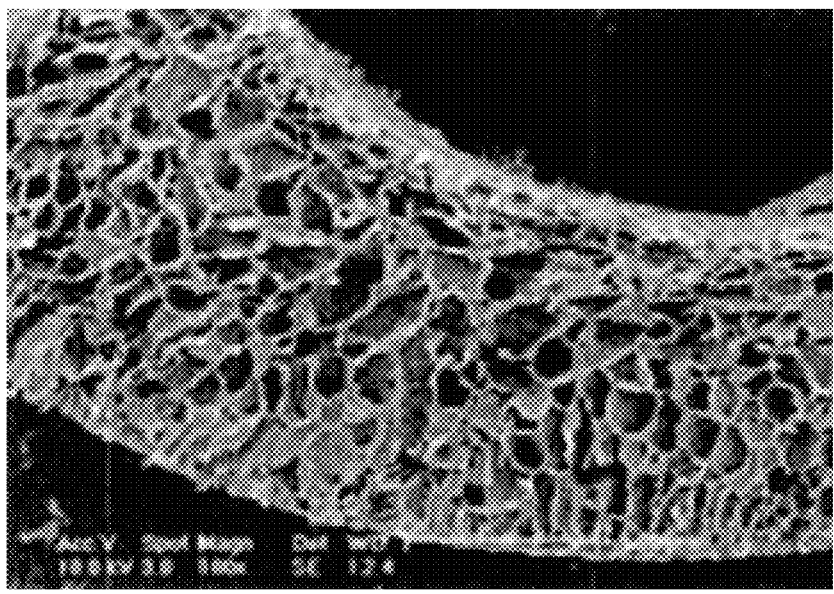
FIGS. 12A through 12E are SEM images of sections under axial temperature gradient at −20° C. for PLLA/benzene solutions with different concentrations (wt/v): (A) cross section, 2.5%; (B) cross section, 5.0%; (C) cross section, 7.5%; (D) cross section, 10.0%; (E) longitudinal section, 7.5%.
Figure 12B:
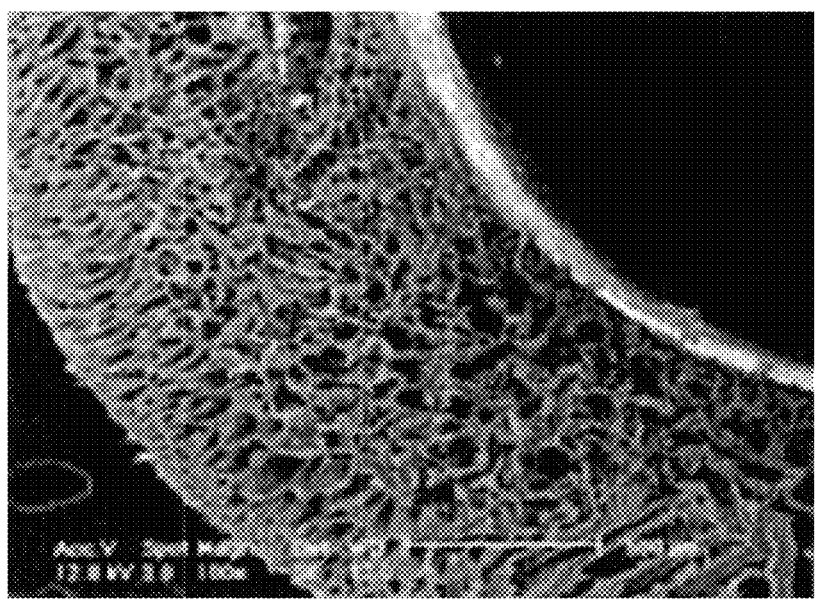
Figure 12C:
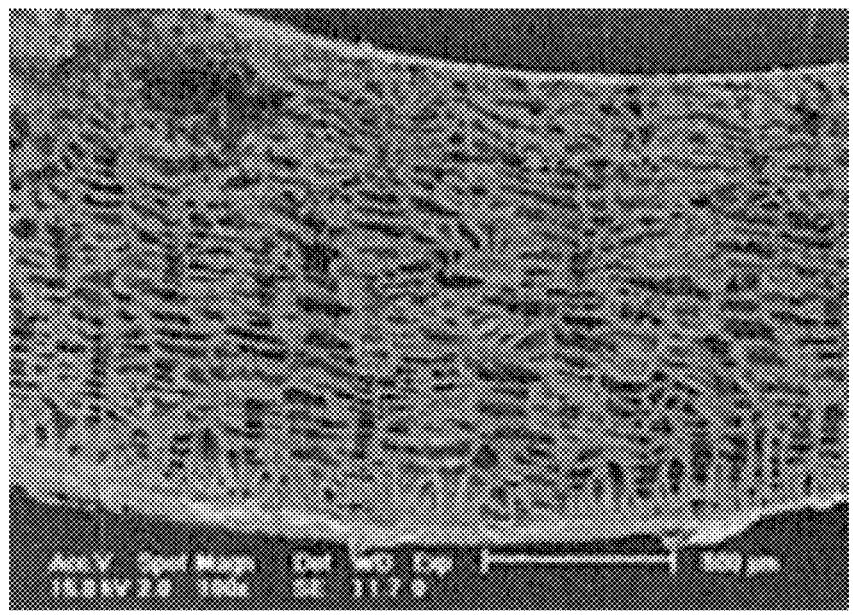
Figure 12D:
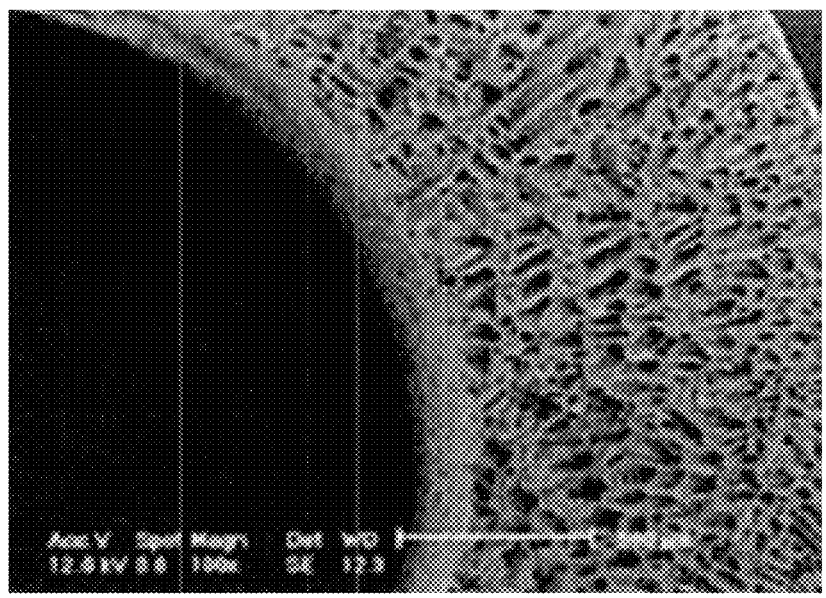
Figure 12E:
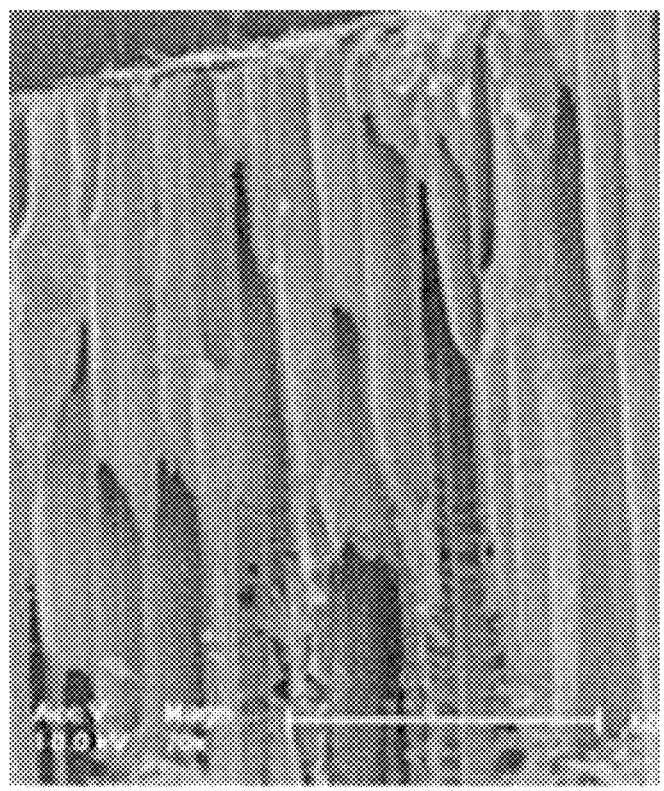

For each scaffold formed in this example, the microtube diameters became radially larger or smaller along the direction of the temperature gradient (results summarized in FIG. 8). The microtube size of the I/O structured gradient scaffold was gradually reduced from 200 µm to nearly zero while that of the O/I structured scaffold was gradually increased from about 30 µm to 200 µm. The microtube size was reduced with increasing polymer concentration (see FIGS. 9 through 11 and Table 1). The radial temperature gradient direction did not significantly affect the average pore size at the same polymer concentration. The pore size formed under the radial temperature gradient was also greatly reduced from 200 µm to 20 µm when the temperature changed from $-20°$ C. to $-196°$ C. (again see FIGS. 9 through 11 and Table 1). The phase separation temperature had no obvious effect on the porosity (Table 1). Furthermore, there was no obvious gradient microtubule structure and no fishbone-like structure under the phase separation temperature of $-196°$ C. (see FIGS. 11A through 11C).

Axial Oriented Scaffold Structure

When the polymer solutions were placed into molds consisting of a steel bottom and PTFE wall/shaft/top, a temperature gradient was formed from bottom to top (from lower temperatures to higher temperatures) and maintained uniaxially during the thermally induced phase separation process. The characteristic architecture of an array of parallel microtubules was achieved (see FIGS. 12A through 12E). When benzene was used as the solvent of poly(L-lactic acid) (PLLA), the cross-sections of the microtubules were polygons with 3-7 sides. When the polymer concentration was increased from 2.5% to 10%, the porosity of the formed scaffolds was slightly reduced from 95% to 90%, and the average pore size was also decreased from the range of 120 µm-150 µm to the range of 80 µm-120 µm.

When phase separation temperature was decreased from $-20°$ C. to $-196°$ C. (using liquid nitrogen), the pore size was greatly decreased from the range of 115 µm-140 µm to the range of 20 µm-40 µm (see Table 1). The phase separation temperature and the direction of temperature gradient both had clear effects on the micro-architecture of the PLLA scaffolds. This was due to the nature of the solid-liquid phase separation, i.e., the crystallization of the solvent, which controls the pore architecture of the formed scaffold. Different directions of the temperature gradient resulted in different crystallization paths of the solvent (benzene). In comparison with the axial temperature gradient, benzene has a shorter crystallization path under the radial temperature gradient due to its thinner wall thickness. Therefore, benzene rapidly crystallized under such an extremely low temperature (i.e., $-196°$ C.) and there likely was not enough time to form the gradient and branched pore structure.

TABLE 1

Structural and mechanical properties of the solid-walled PLLA scaffolds

| Polymer | Solvent | Conc. (wt/v, %) | Phase sep. temp. (° C.) | Pore structure | Density (g/cm³) | Porosity (%) | Pore Size (µm) | Compressive modulus (MPa) axial | Compressive modulus (MPa) radial | Compressive yield strength (MPa) axial | Compressive yield strength (MPa) radial |
|---|---|---|---|---|---|---|---|---|---|---|---|
| PLLA | Benzene | 2.5 | −20 | ◄ | 0.064 | 94.9 | 0-200 | — | — | — | — |
| PLLA | Benzene | 2.5 | −20 | ► | 0.063 | 95.0 | 0-210 | — | — | — | — |
| PLLA | Benzene | 2.5 | −20 | ▲ | 0.065 | 94.8 | 120-150 | 0.55 | 0.32 | 0.22 | 0.13 |
| PLLA | Benzene | 5.0 | −20 | ◄ | 0.098 | 92.2 | 0-150 | 1.7 | 4.9 | 0.16 | 0.40 |

TABLE 1-continued

Structural and mechanical properties of the solid-walled PLLA scaffolds

| Polymer | Solvent | Conc. (wt/v, %) | Phase sep. temp. (° C.) | Pore structure | Density (g/cm³) | Porosity (%) | Pore Size (µm) | Compressive modulus (MPa) | | Compressive yield strength (MPa) | |
|---|---|---|---|---|---|---|---|---|---|---|---|
| | | | | | | | | axial | radial | axial | radial |
| PLLA | Benzene | 5.0 | LN | ◄ | 0.096 | 92.4 | 10-20 | 2.1 | 5.2 | 0.20 | 0.45 |
| PLLA | Benzene | 5.0 | −20 | ► | 0.097 | 92.3 | 0-155 | 1.8 | 4.5 | 0.17 | 0.43 |
| PLLA | Benzene | 5.0 | LN | ► | 0.094 | 92.5 | 10-20 | 2.0 | 5.0 | 0.21 | 0.48 |
| PLLA | Benzene | 5.0 | −20 | ▲ | 0.102 | 91.9 | 115-140 | 3.8 | 2.0 | 0.38 | 0.15 |
| PLLA | Benzene | 5.0 | LN | ▲ | 0.101 | 92.0 | 20-40 | 4.2 | 2.9 | 0.43 | 0.23 |
| PLLA | Benzene | 7.5 | −20 | ◄ | 0.123 | 90.2 | 0-120 | 2.6 | 6.3 | 0.27 | 0.53 |
| PLLA | Benzene | 7.5 | −20 | ► | 0.125 | 90.1 | 0-120 | 2.5 | 5.9 | 0.24 | 0.56 |
| PLLA | Benzene | 7.5 | −20 | ▲ | 0.125 | 90.1 | 90-130 | 4.5 | 2.8 | 0.44 | 0.21 |
| PLLA | Benzene | 10.0 | −20 | ◄ | 0.133 | 89.4 | 0-100 | 3.6 | 8.4 | 0.37 | 0.85 |
| PLLA | Benzene | 10.0 | −20 | ► | 0.135 | 89.3 | 0-100 | 3.9 | 8.7 | 0.40 | 0.88 |
| PLLA | Benzene | 10.0 | −20 | ▲ | 0.131 | 89.6 | 80-120 | 7.7 | 4.0 | 0.68 | 0.34 |

Figure 13:
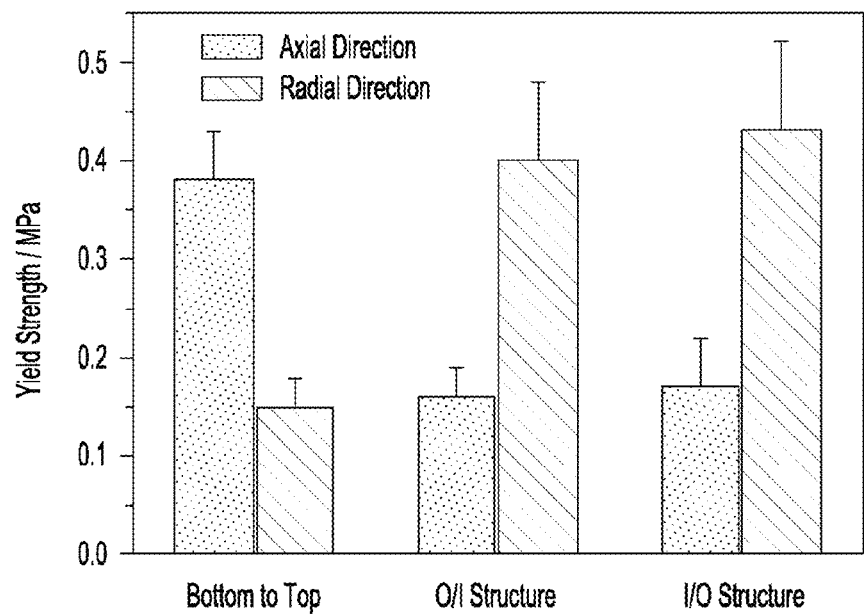
FIG. 13 is a graph illustrating the compressive yield strength of PLLA scaffolds prepared with benzene as the solvent, PLLA concentration of 5.0%, and phase separation temperature of −20° C.

◄: O/I oriented structure;
►: I/O oriented structure;
▲: bottom-top oriented structure Mechanical Properties The mechanical properties, including compressive modulus and compressive yield strength, are shown in Table 1. The typical results on the compressive yield strength are presented in FIG. 13.

For the scaffolds possessing oriented gradient microtubules, the anisotropic architecture led to anisotropic mechanical properties. Both the compressive modulus and the yield strength of a scaffold with a microtubular architecture were significantly greater in the longitudinal direction than in the transverse direction of the tubular structure (see Table 1 & FIG. 13). Both the compressive modulus and the compressive yield strength increased with polymer concentration as expected (again see Table 1 and FIG. 13). At the same polymer concentration, there was no statistical difference in the mechanical properties between the two types of radially oriented gradient (O/I or I/O) scaffolds.

Subcutaneous Implantation and Cellular Migration into the Scaffolds In Vivo

To investigate cell migration into and distribution within the scaffolds of different pore structures in vivo, scaffolds with radially oriented and non-oriented pores (i.e., comparative example formed according to the method described in this example expect molds of the same material were used so random pores were generated) were subcutaneously implanted into mice. The tubular scaffolds (2 mm in thickness) were implanted into subcutaneous pockets of 6-8 weeks old C57BL/6 male mice (Charles River Laboratories, Wilmington, Mass.). Surgery was performed under general inhalation anesthesia with isofluorane. Two midsagittal incisions were made on the dorsa and one subcutaneous pocket was created on each side of each incision using blunt dissection. One scaffold was implanted subcutaneously into each pocket. Four samples were implanted for each group. After placement of implants, the incisions were closed with staples. At the end of 2 weeks of implantation period, the mice were euthanized and the implants were harvested.

Figure 14A:
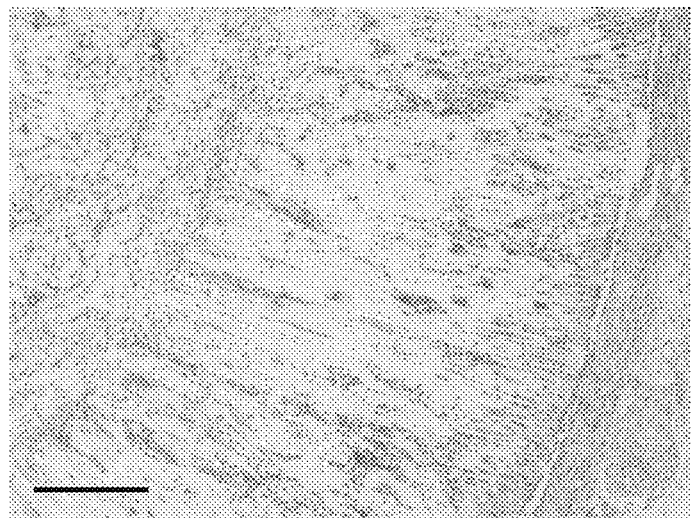
FIGS. 14A and 14B are SEM images of a tubular scaffold with gradient and radially oriented microtubular pores (FIG. 14A) and a control scaffold (FIG. 14B, with non-oriented pores) after 2 weeks of implantation, H-E staining of the cross sections of implants showed that abundant host cells migrated into the scaffolds with orientated pores and the fibroblast-like cells appeared healthy in the micro-channels (FIG. 14A), and substantially fewer cells migrated into the control scaffolds with non-oriented pores (FIG. 14B) (scale bar: 200 μm)
Figure 14B:
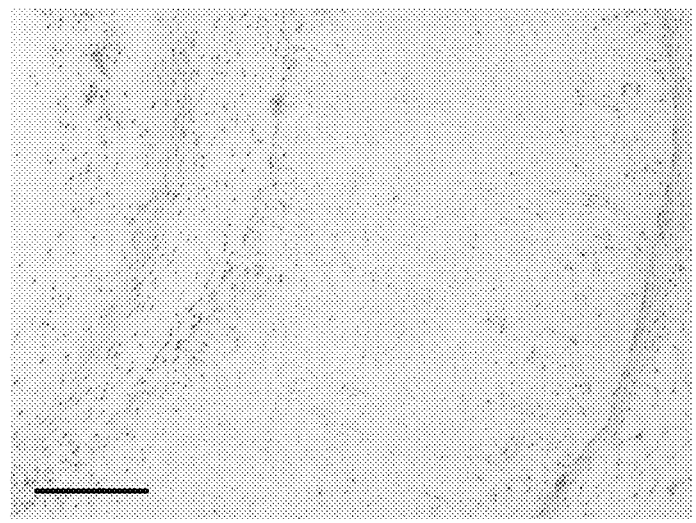
Figure 15A:
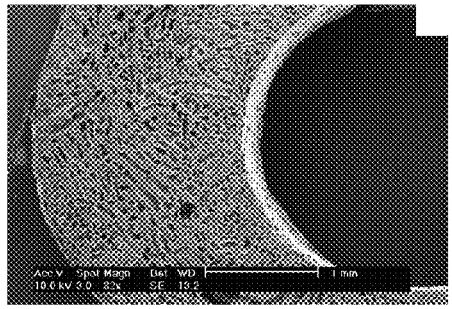
FIGS. 15A through 15I are SEM images of PLLA scaffolds prepared using PLLA solutions in benzene and THF, (FIGS. 14A-C) 7.5% (wt/v) PLLA/(benzene/THF) and benzene/THF (v/v)=9:1, (D-F) 7.5% (wt/v) PLLA/(benzene/THF) and benzene/THF (v/v)=8:2.
Figure 15B:
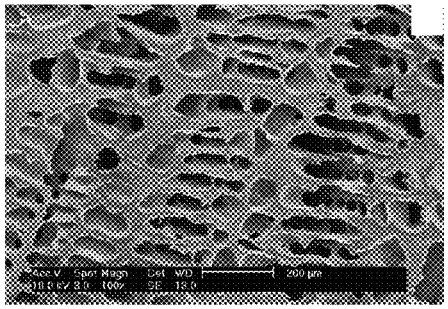
Figure 15C:
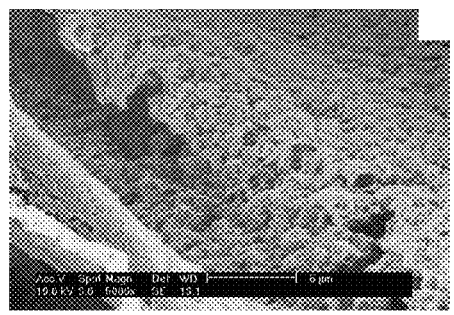
Figure 15D:
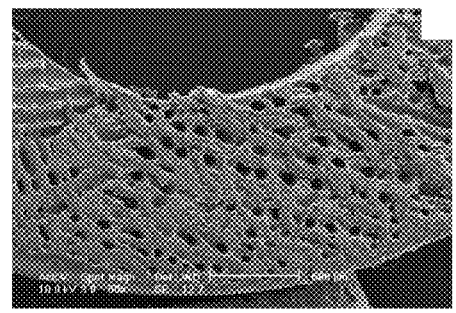
Figure 15E:
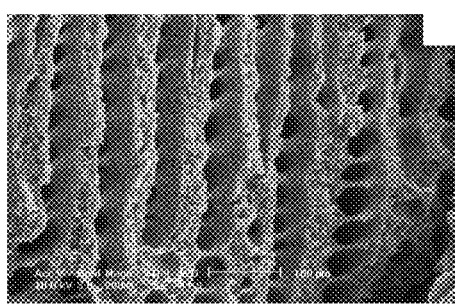
Figure 15F:
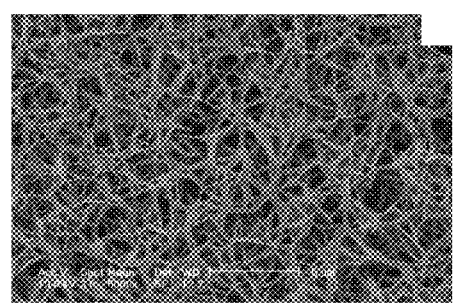
Figure 15G:
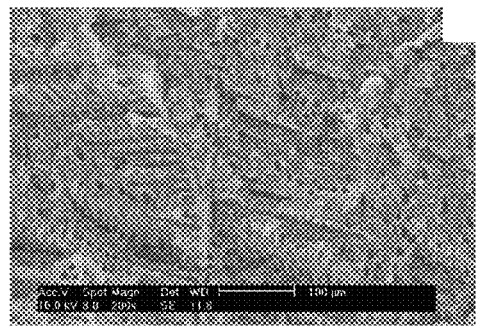
Figure 15H:
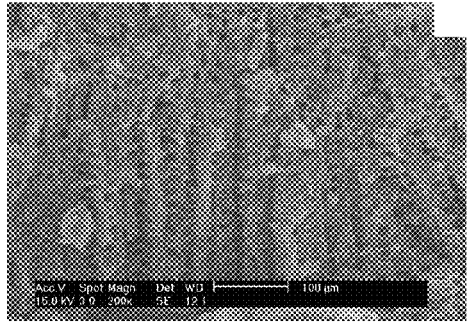
Figure 15I:
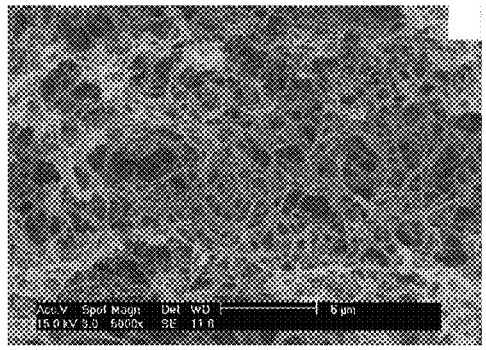

H-E staining of the cross sections of implants showed that abundant host cells migrated into the scaffolds with orientated pores and the fibroblast-like cells appeared healthy in the micro-channels (see FIG. 14A). In contrast, substantially fewer cells migrated into the scaffolds with non-oriented pores (see FIG. 14B). Both types of the scaffolds maintained geometrical shape and structural integrity during the 2-week implantation.

Example 2

Vessel Scaffold Fabrication

For the preparation of nano-fibrous PLLA scaffolds, benzene and THF with various ratios were used as mixed solvents. Comparative PLLA scaffolds were made using THF as the solvent alone. After the phase separation (performed in the same manner described for Example 1), the molds containing the polymer solutions were immersed into cold hexane for 2 days to extract the solvents, changing the hexane three times a day. Hexane was then exchanged with cyclohexane. The polymer scaffolds were removed from the cyclohexane, and were frozen at −70° C. for at least 5 hours. The frozen scaffolds were lyophilized at −10° C. for 72 hours and then kept in a desiccator until usage.

Results

Figure 16A:
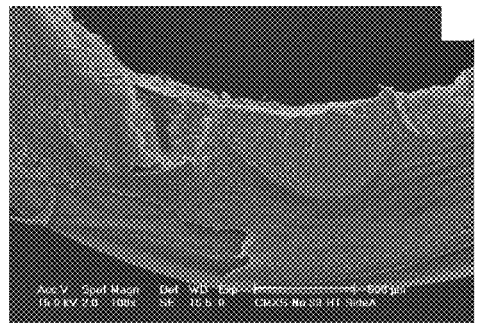
FIGS. 16A and 16B are SEM images of comparative PLLA scaffolds prepared using 7.5% (wt/v) PLLA/(THF), the phase separation temperature was −20° C.
Figure 16B:
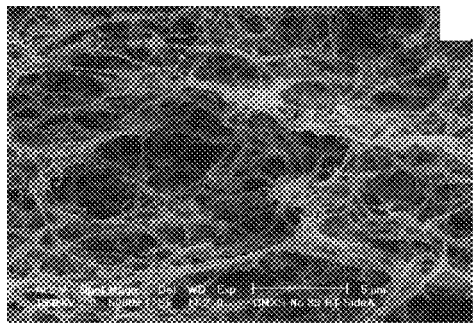
Figure 17A:
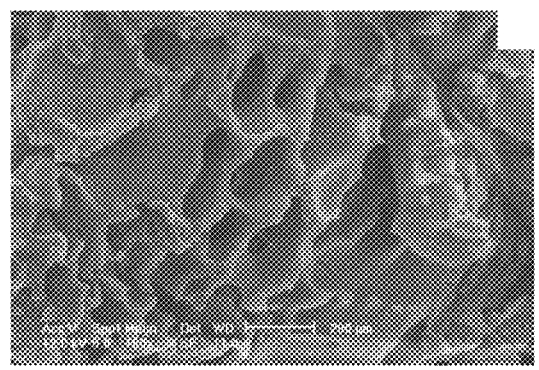
FIGS. 17A through 17D are SEM images of PLLA scaffolds prepared with various polymer concentrations using a thermally induced phase separation technique (benzene/THF=8:2, PLLA concentration (wt/v): (A) 2.5%, (B:) 5.0%, (C) 7.5%, and (D) 10.0%, where the phase separation temperature was −20° C.
Figure 17B:
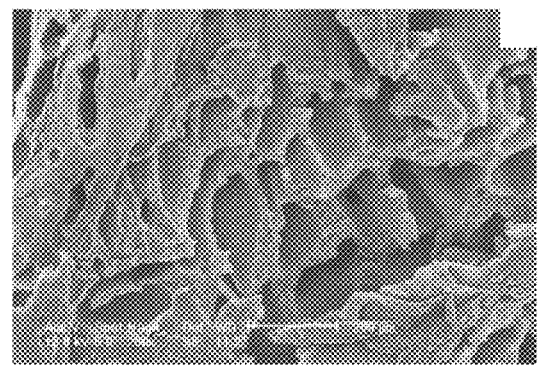
Figure 17C:
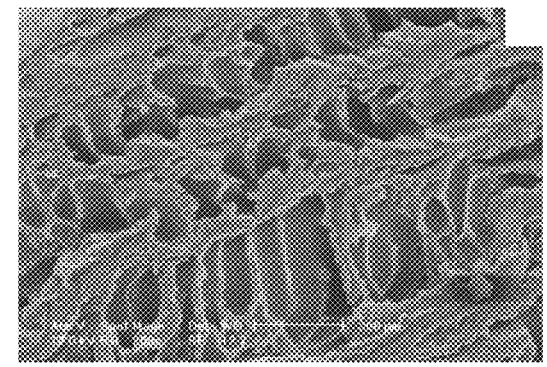
Figure 17D:
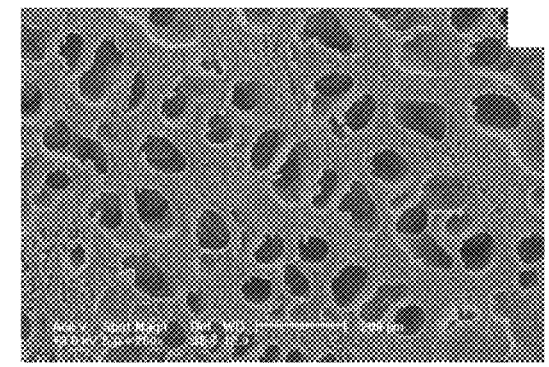

The benzene/tetrahydrofuran (THF) mixture resulted in the creation of a nano-fibrous scaffold with oriented and interconnected microtubules (see FIGS. 15A through 15I). When the solvent was THF alone, the scaffold was composed of nano-fibers, but few micro-sized pores (see FIGS. 16A and 16B).

When benzene and THF were mixed at various ratios, nano-fibrous matrices with oriented microtubules on the micrometer scale were created. Similar to the scaffold made from PLLA/benzene solution (in Example 1), these scaffolds had low densities and high porosities. The density increased and the porosity decreased with increasing polymer concentration. When benzene/THF ratio was 9/1 (v/v), the diameter of the microtubule ranged from about 80 µm to 250 µm. A partly nano-fibrous structure was formed in these microtubule walls and the average diameter of the nano-fibers was 165±15 nm. When the ratio of benzene/THF was 8:2 (v/v) and 6:4 (v/v), complete nano-fibrous structures were achieved (see FIGS. 15D through 15I). The average fiber diameter of the fibrous matrices did not change statistically with the concentration of the polymer or the ratio of benzene/THF. In fact, the fiber diameter was similar to that of the nano-fibrous PLLA matrices fabricated using THF alone. However, the size of the microtubules was greatly reduced with further increase of THF percentage in the solvent mixture.

Figure 18A:
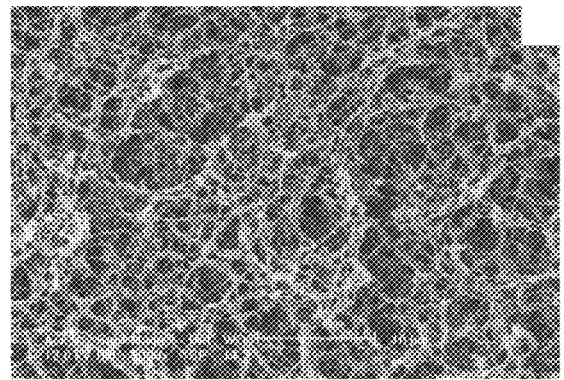
FIGS. 18A through 18C are SEM images of PLLA scaffolds (benzene/THF=8:2 and PLLA concentration 5.0% (wt/v) formed with different phase separation temperatures, (A) −20° C., (B) −80° C., and (C) −196° C.
Figure 18B:
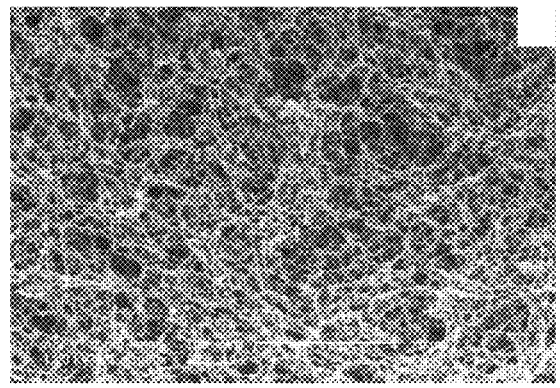
Figure 18C:
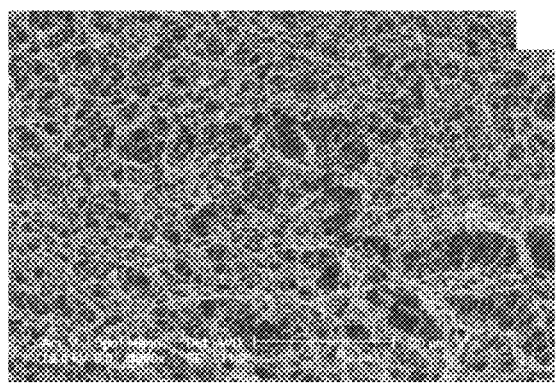

At the same benzene/THF ratio, the pore size decreased with decreasing temperature (see Table 2) and increasing polymer concentration (see FIGS. 17A through 17D and Table 2), although the diameter of the nano-fibers did not change appreciably with the temperature (see FIGS. 18A through 18C and Table 2). For the benzene/THF ratio range studied, the microtubules with nano-fibrous walls were highly interconnected "tunnels" in the scaffolds, and the "tunnels" were also oriented in the orthogonal directions.

Mechanical Properties

Figure 19:
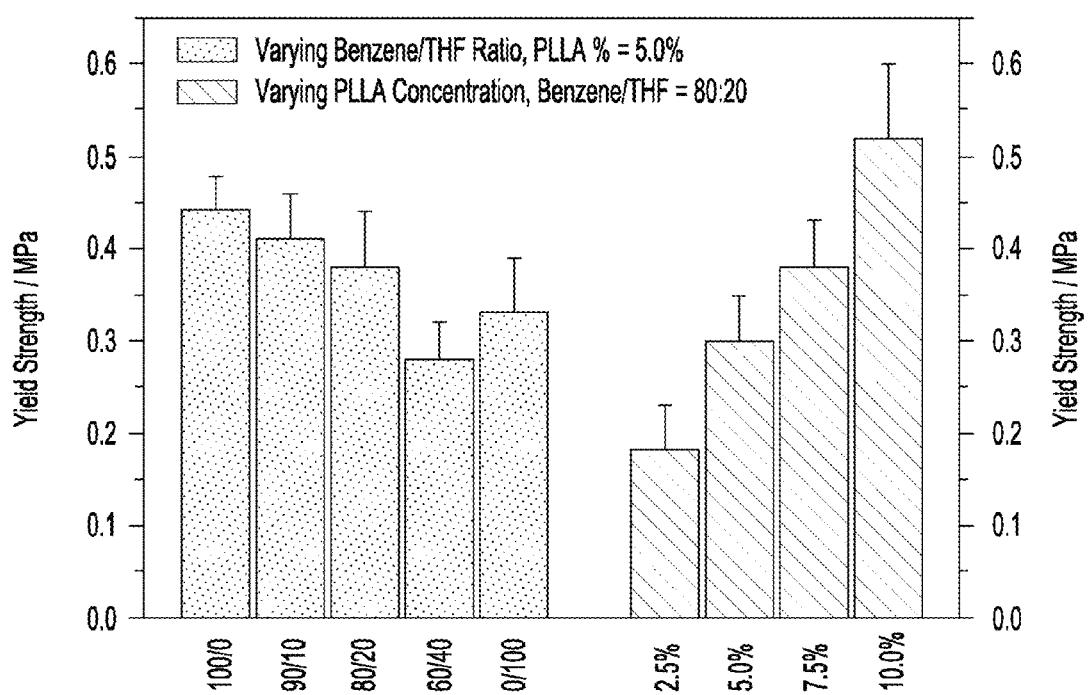
FIG. 19 is a graph illustrating the compressive yield strength of PLLA scaffolds prepared with PLLA solutions in benzene, THF, and their mixtures using a thermally induced phase separation technique with a temperature of −20° C.

The mechanical properties, including compressive modulus and compressive yield strength, are shown in Table 2. The typical results on the compressive yield strength are presented in FIG. 19.

Compressive modulus and compressive yield strength of the nano-fibrous scaffolds with interconnected channels were both slightly lower than those of the scaffolds with a solid-walled oriented gradient structure (compare Table 1 of Example 1 with Table 2) at the same polymer concentration in the oriented direction of microtubules. At similar polymer concentrations, the scaffolds with a solid-walled structure (Example 1) had larger average pore size and higher skeletal density of the pore walls, which may have led to the higher compressive modulus and yield strength. The average pore size became smaller as the THF was introduced and increased, resulting in the looser aggregation of nano-fibers in the pore walls, which might also be associated with the lower compressive modulus and yield strength.

molds then transferred into a freezer set to a predetermined temperature to induce phase separation. The phase-separated polymer/solvent system was then transferred into a freeze drying vessel at a temperature ranging from −5° C. to −10° C. in an ice/salt bath, and was freeze-dried under vacuum (pressure lower than 0.5 mmHg) for 72 hours. The dried scaffolds were then kept in a desiccator until characterization or usage.

For the porous nano-fibrous scaffolds, THF was used as the solvent. A sugar template was introduced before the phase separation and then was leached out to create the highly porous and interconnected pore structure.

Electrospun/TIPS Composites Blood Vessel Scaffolds

Four types of the electrospun/TIPS composites blood vessel scaffolds were prepared. The electrospun layer was used as the inner layer, the outer layer, both the inner and outer layers, and a middle layer (see FIGS. 6A through 6D). By assembling the electrospun and TIPS layers, E(electrospun)/T(TIPS) composite structures, T/E composite structures, E/T/E composite structures, and T/E/T composite structures were made. When the electrospun layer is formed on an outer wall, the phase-separated scaffold is produced and then the layer is electrospun on the outer layer of the scaffold(s). When the electrospun layer is formed on an inner wall or as a middle layer, the electrospun tube is formed first and then is assembled into the mold before casting the porogen materials and polymer solution therein.

Figure 20A:
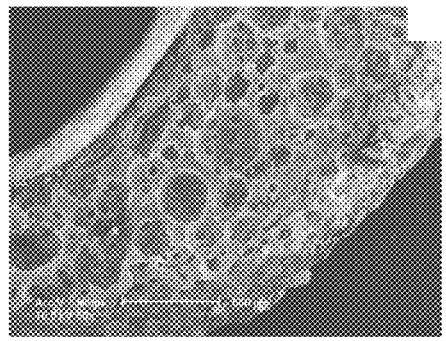
FIGS. 20A through 20O are SEM images illustrating the morphologies of the multilayered blood vessel scaffolds.
Figure 20B:
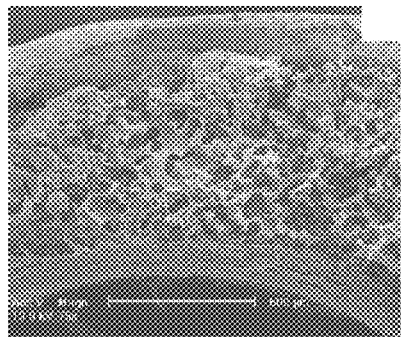
Figure 20C:
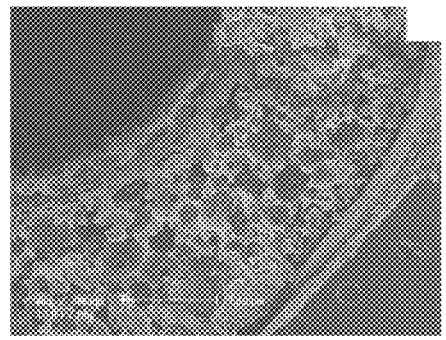
Figure 20D:
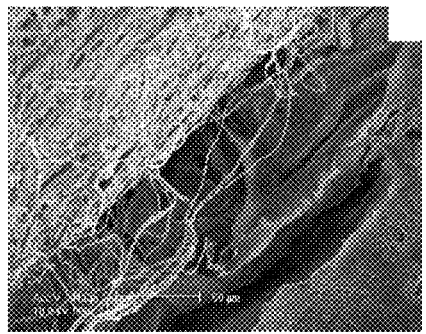
Figure 20E:
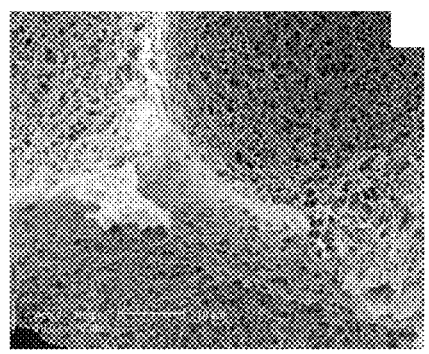
Figure 20F:
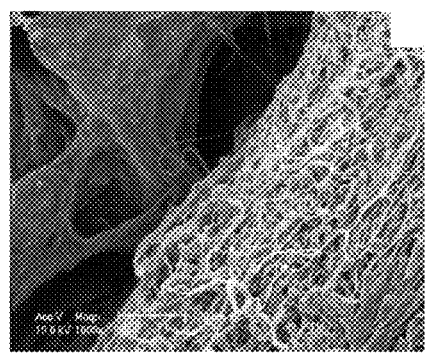
Figure 20G:
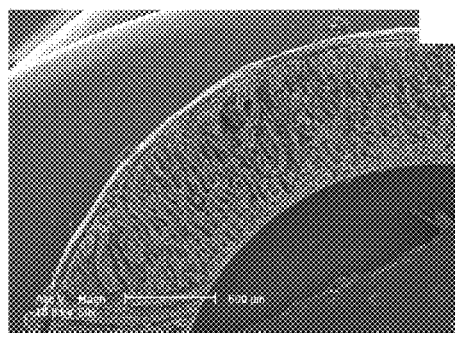
FIGS. 20G-L are solid-wall porous scaffolds where G, H, and I illustrate electrospun/thermally induced phase separation (E/T), E/T/E and T/E multilayered structures, where J illustrates the interface of the E/T composite scaffold, where K illustrates the solid-wall structure in the TIPS layer, and where L illustrates the interface of the T/E composite scaffold.
Figure 20H:
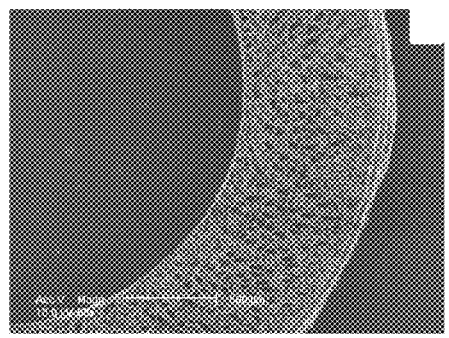
Figure 20I:
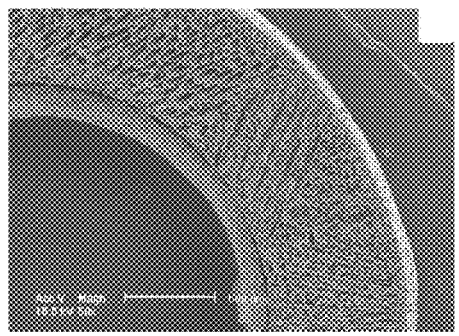
Figure 20J:
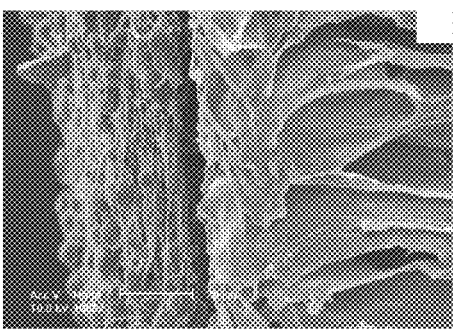
Figure 20K:
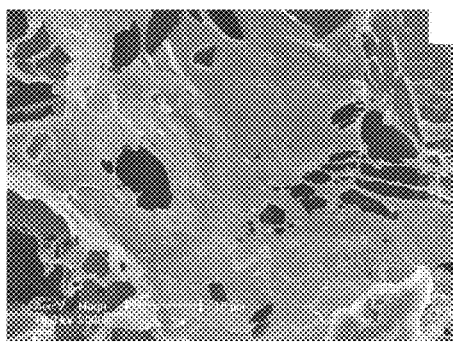
Figure 20L:
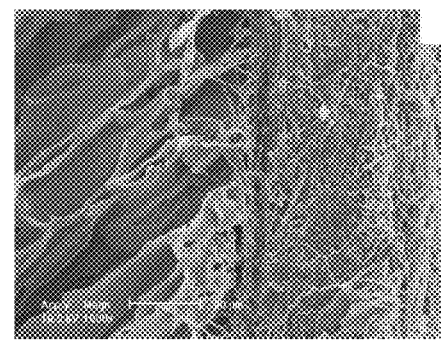
Figure 20M:
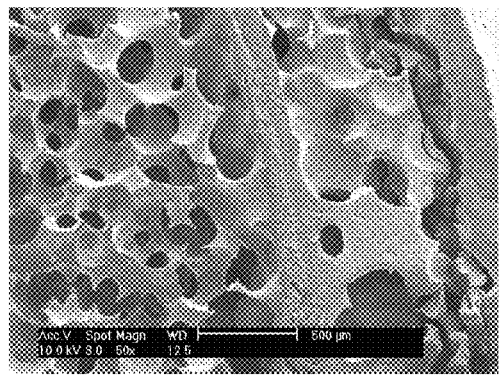
Figure 20N:
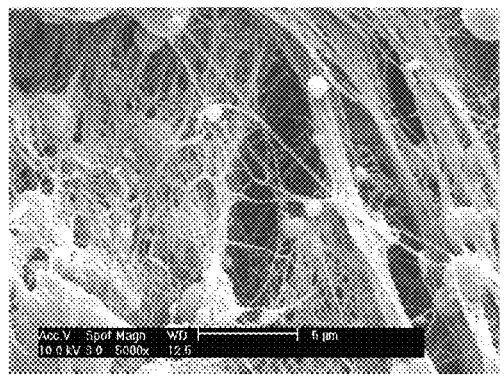
Figure 20O:
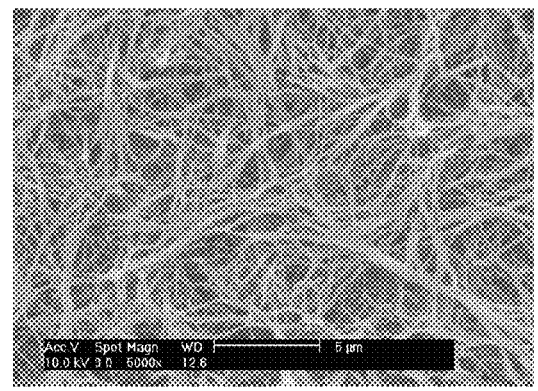

The morphologies of the three types of multilayered composite blood vessel scaffolds are shown in FIGS. 20A through 20O. The electrospun inner or outer layer, as well as the TIPS porous layer can be clearly seen. The electrospun PCL layer

TABLE 2

Structural and mechanical properties of the nano-fibrous PLLA scaffolds

| Polymer | Solvent (Benzene/THF) | Conc. (wt/v %) | Phase separation temp. (° C.) | Density (g/cm³) | Porosity (%) | Pore Size (μm) | Fiber Diameter (nm) | Comp. modulus (MPa) | Comp. yield strength (MPa) |
|---|---|---|---|---|---|---|---|---|---|
| PLLA | 100/0 | 7.5 | −20 | 0.125 | 90.1 | 120 ± 16 | — | 4.5 | 0.44 |
| PLLA | 90/10 | 7.5 | −20 | 0.102 | 91.9 | 107 ± 15 | 165 ± 15 | 4.2 | 0.41 |
| PLLA | 80/20 | 2.5 | −20 | 0.048 | 96.2 | 153 ± 25 | 158 ± 20 | 0.5 | 0.18 |
| PLLA | 80/20 | 5.0 | −20 | 0.065 | 94.8 | 126 ± 18 | 155 ± 18 | 2.9 | 0.30 |
| PLLA | 80/20 | 7.5 | −20 | 0.093 | 92.6 | 80 ± 7 | 157 ± 21 | 3.5 | 0.38 |
| PLLA | 80/20 | 10.0 | −20 | 0.110 | 91.3 | 77 ± 9 | 160 ± 31 | 6.4 | 0.52 |
| PLLA | 80/20 | 5.0 | −80 | 0.069 | 94.5 | 115 ± 20 | 158 ± 20 | 3.2 | 0.33 |
| PLLA | 80/20 | 5.0 | LN | 0.068 | 94.6 | 52 ± 12 | 154 ± 23 | 3.3 | 0.32 |
| PLLA | 60:40 | 7.5 | −20 | 0.091 | 92.8 | 20 ± 3 | 143 ± 20 | 3.0 | 0.28 |
| PLLA | 0/100 | 7.5 | −20 | 0.094 | 92.5 | — | 144 ± 22 | 3.0 | 0.38 |

Example 3

Electrospun Blood Vessel Scaffolds

A polymer solution was prepared by dissolving poly(ε-caprolactone) (PCL) in dichloromethane/acetone (2:1 volume ratio) at the concentration of 12.5%. A voltage of 15 kV was applied by a voltage regulated DC power supply to generate the polymer jet. The resulting PCL fibers were collected on a rotating collector with a constant rotating speed to form a vessel.

Thermally Induced Phase Separation (TIPS) Blood Vessel Scaffolds

Specific molds were designed to fabricate the blood vessel scaffold with porous structures. The molds were composed of top and bottom plates, inner shaft and outer cylinder made entirely of PTFE. The molds each had an inner-diameter of 2.00 mm and an outer-diameter of 3.00 mm.

For the porous solid-walled scaffolds, dioxane was used as the solvent. The polymer solutions were poured into the can provide good elasticity and mechanical strength. The TIPS layers are highly porous and interconnected, which can enhance the cell growth and mass transport.

Example 4

In this example, 3D nano-fibrous scaffolds were compared with 3D solid-wall scaffolds and nano-fibrous thin matrices were compared with flat films without nano-fibrous features. This was accomplished to test the effect of nano-fibrous tubular scaffolds on phenotype control of human aortic smooth muscle cells.

Fabrication of Nano-Fibrous Matrices, Flat Films and 3D Tubular Scaffolds

Poly-L-lactide (PLLA) with an inherent viscosity of approximately 1.6 was used in each of the structures.

For the nano-fibrous (NF) matrices and the flat films, the PLLA was dissolved in tetrahydrofuran (THF) (10% wt/v) at 60° C. and cast into a pre-heated glass mold. The mold was quickly sealed using a cover glass. The PLLA solution was phase separated at −20° C. for 2 hours and then immersed into an ice/water mixture to exchange THF for 24 hours. The matrices were washed with distilled water at room temperature for 24 hour. The obtained thin sheets of nano-fibrous matrices (having a thickness of about 40 μm) were then vacuum-dried for 2 days. The flat films were fabricated in a similar manner excluding the phase separation step. Instead, the solvent was evaporated at room temperature in a fume hood.

In this example, the fabrication of the 3D tubular nano-fibrous scaffolds was accomplished by preparing a PLLA/THF (10% wt/v) solution, and casting the solution into an assembled sugar template (formed from bound sugar spheres, 125-250 μm in diameter) under a mild vacuum. The polymer-sugar composite was phase separated at −20° C. overnight and was then immersed into cyclohexane to exchange THF for 2 days. The resulting composites were freeze-dried and the sugar spheres were leached out in distilled water, and freeze-dried again to obtain highly porous scaffolds. The highly porous tubular scaffolds had inner diameters of about 3 mm and outer diameters of about 5 mm. The tubular scaffolds were cut into 4 mm long tubes before cell seeding.

For cell culture studies, nano-fibrous PLLA scaffolds with interconnected spherical pore structure were prepared in Teflon vials as described above and then were cut into circular disks with dimensions of 3.6 mm in diameter and 1 mm in thickness. For both cell culture and implantation studies, the scaffolds were sterilized with ethylene oxide.

The solid-wall scaffolds were prepared using a more conventional thermally induced phase separation technique.

Cell Culture and Subcutaneous Implantation

Adult primary human aortic smooth muscle cells (HASMCs) were obtained from Lonza (Walkersville, Md.). The cells were maintained in smooth muscle growth medium-2 (Lonza) at 37° C. in a humidified incubator containing 5% $CO_2$.

The NF matrices or flat films were cut into circular shapes that fit into 12-well plates. The materials were soaked in 70% ethanol for 30 minutes, washed three times with PBS for 30 minutes each, and twice in the cell culture medium for 1 hour each on an orbital shaker at 75 rpm. HASMCs were seeded at a density of $1\times10^4$ cells/cm$^2$ under static conditions. The medium was changed every two days.

The 3D scaffolds (both nano-fibrous and solid-walled) were soaked in 70% ethanol for 30 minutes, washed three times with PBS for 30 minutes each, and twice in the cell culture medium for 2 hours each on an orbital shaker at 75 rpm. $0.5\times10^6$ cells were seeded into each scaffold. After 2 hours of initial seeding, the cell-seeded scaffolds were further cultured for 22 hours under static condition. After that, the cell-seeded scaffolds were transferred to 6-well plates with 5 mL medium per well on an orbital shaker at 75 rpm. The medium was changed twice a week.

After the HASMCs were seeded and cultured on the respective structures (i.e., flat films, NF matrices, tubular scaffolds) for 24 hours, the structure-cell constructs or blank scaffolds (pre-treated in the same way as cell-containing constructs but without cell seeding) were implanted into subcutaneous pockets of nude mice. For implantation surgery, 6-8 wk old male nude mice (Charles River Laboratories, Wilmington, Mass.) were used. Surgery was performed under general inhalation anesthesia with isofluorane. Two midsagittal incisions were made on the dorsa and one subcutaneous pocket was created on each side of each incision using blunt dissection. One scaffold-cell construct or blank scaffold was implanted subcutaneously into each pocket at random. Four samples were implanted for each group. After placement of implants, the incisions were closed with staples. At the end of 2 week of implantation period, the mice were euthanized and the implants were harvested.

Scanning Electron Microscopy (SEM) Observation

Blank samples were sputter-coated with gold before SEM observation. Samples with cells were first rinsed in PBS, fixed in 2.5% glutaraldehyde and 2% paraformaldehyde overnight, and post-fixed in 1% osmium tetroxide for 1 hour. Samples were dehydrated in increasing concentrations of ethanol and hexamethyldisilizane. The samples were then sputter-coated with gold and observed under a scanning electron microscope (Philips XL30 FEG).

Gene Expression Analysis

Total cellular RNA from each experimental group at a pre-determined time was extracted using the RNeasy mini kit (Qiagen, Valencia, Calif.) according to the manufacturer's instructions and treated with DNase I (Qiagen). cDNA was synthesized with superscript III first-strand synthesis system (Invitrogen, Carlsbad, Calif.). Polymerase chain reaction (PCR) amplification was performed with primers for smooth muscle myosin heavy chain (SMMHC), Smoothelin and Myocardin (MyoCD) using SYBR Green supermix kit (Bio-rad, Hercules, Calif.) following the instructions. PCR primers and reaction conditions are described in Table 3. All RNA samples were adjusted to yield equal amplification of 18S RNA as an internal standard.

TABLE 3

Primers used for qRT-PCR

| Gene | Primer sequence | GeneID | Product size (bp) |
|---|---|---|---|
| 18S RNA | forward: 5'-ggaagggcaccaccaggagt-3' (SEQ. 1D NO. 1)<br>reverse: 5'-tgcagccccggacatctaag-3' (SEQ. 1D NO. 2) | 100008588 | 317 |
| MyoCD | forward: 5'-ctgggacgacatggaaaa-3' (SEQ. 1D NO. 3)<br>reverse: 5'-acatggctgggacattga-3' (SEQ. 1D NO. 4) | 93649 | 191 |
| SMMHC | forward: 5'-agagacagcttcacgagtatgag-3' (SEQ. 1D NO. 5)<br>reverse: 5'-cttccagctctctttgaaagtc-3' (SEQ. 1D NO. 6) | 4629 | 398 |
| Smoothelin | forward: 5'-cctggatacagaggacatgg-3' (SEQ. 1D NO. 7)<br>reverse: 5'-caggtggttgtagagcgact-3' (SEQ. 1D NO. 8) | 6525 | 157 |

Histological Analysis

Constructs were washed in PBS, fixed with 3.7% formaldehyde in PBS overnight, dehydrated through a graded series of ethanol, embedded in paraffin, and sectioned at a thickness of 5 μm. Sections were deparaffinized, rehydrated with a graded series of ethanol, and stained with H-E or Masson's trichrome method. For immunohistochemical (IHC) analysis, following deparaffinization of sections, slides were placed in 10 mM citrate buffer for antigen unmasking. After rinsing in deionized water, quenching of endogenous peroxidase activity was achieved by incubating sections in 3% hydrogen peroxide for 10 minutes. After washing with deionized water and blocking with serum, tissue sections were incubated with primary antibodies to smooth muscle alpha-actin (SM-α-actin) (Millipore, Temecula, Calif.) or human mitochondria (Abcam, Cambridge, Mass.). Following a PBS rinse, sections were then incubated with biotinylated-secondary antibodies, followed by avidin-biotin complex staining (Vector labs, Burlingame, Calif.).

Statistical Analysis

Numerical data were reported as mean±S.D. (n=3). A value of $p<0.05$ was considered to be statistically significant.

Results

Phenotype Control of HASMCs on PLLA Flat Films and NF Matrices

Figure 21A:
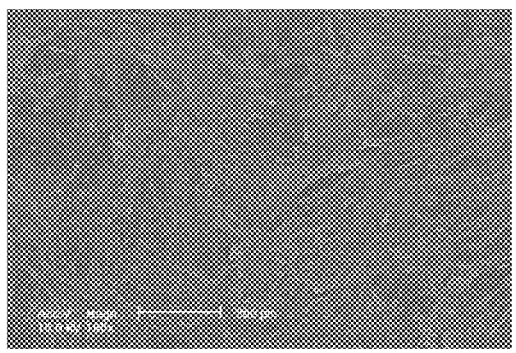
FIGS. 21A and 21B are SEM micrographs of human aortic smooth muscle cells (HASMCs) cultured on PLLA flat films (A) and NF matrices (B) after 24 hr of seeding and culture.
Figure 21B:
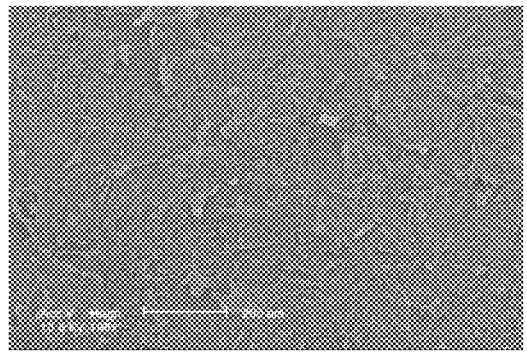
Figure 22:
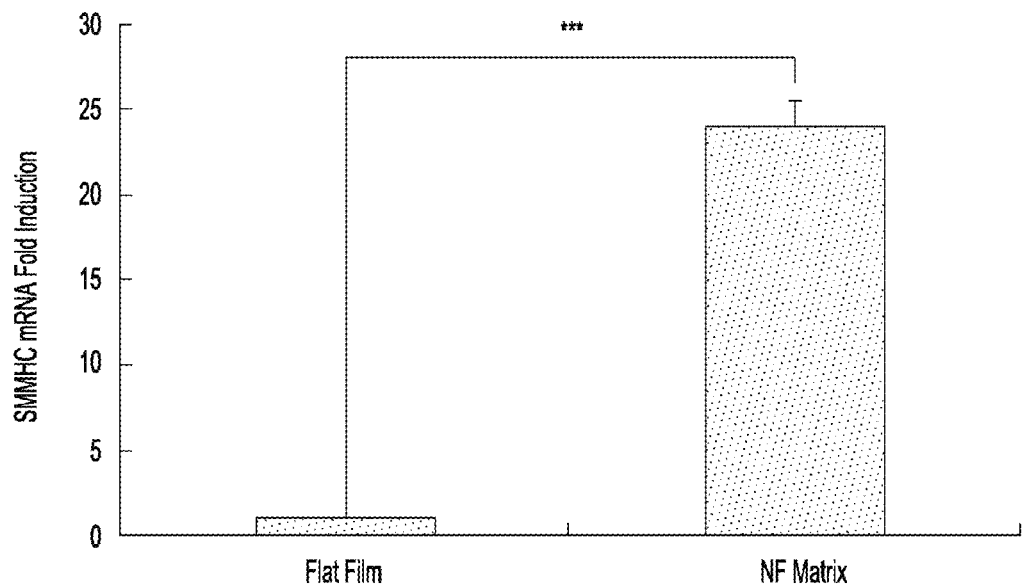
FIGS. 22 through 24 are graphs illustrating the gene expression of smooth muscle cell (SMC) specific markers on flat films or NF matrices after 6 days of culture, ***P<0.001.
Figure 23:
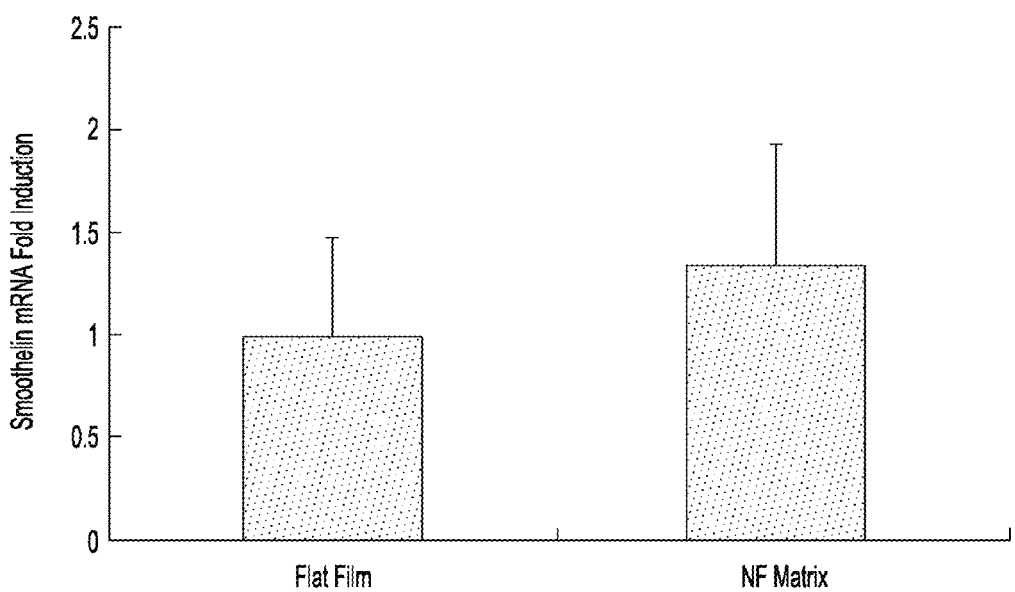
Figure 24:
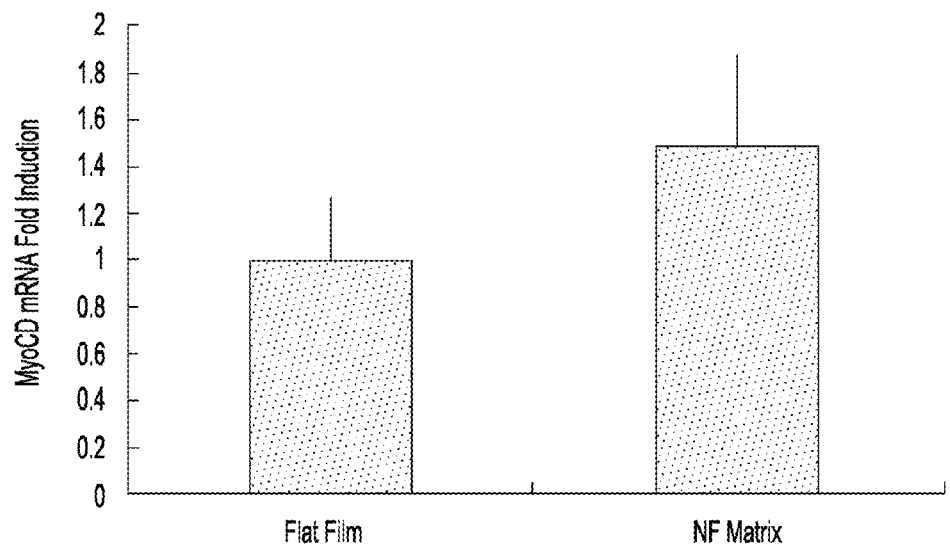

The HASMCs spread over a larger surface area on PLLA flat films (FIG. 21A) after 24 hours of seeding and culture. In contrast, the cells showed a more rounded shape over a smaller surface area when cultured on NF matrices (FIG. 21B). The expression levels of smooth muscle cells (SMCs) contractile phenotype-related genes were quantified. It was found that after 6 days of culture, SMMHC gene expression level was much higher for cells cultured on NF matrices compared to cells cultured on flat films (FIG. 22), while there was no significant difference in the expression levels of Smoothelin (FIG. 23) and MyoCD genes (FIG. 24).

In Vitro Culture of HASMCs on Tubular NF Scaffolds

Figure 25A:
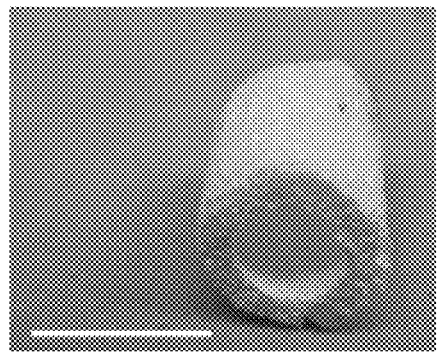
FIG. 25A is a photograph of a tubular NF scaffold (scale bar: 5 mm)
Figure 25B:
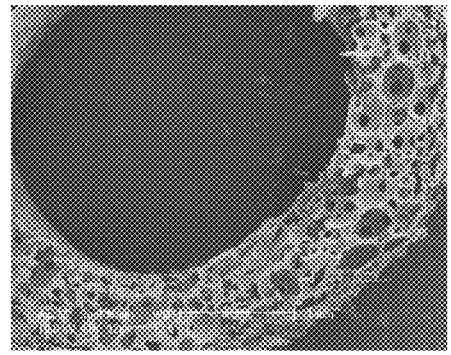
FIGS. 25B through 25D are SEM images of cross-sections of the scaffold of FIG. 25A showing gross structures (B), macro-pores, pore interconnections (C), and nano-fibrous structure (D)
Figure 25C:
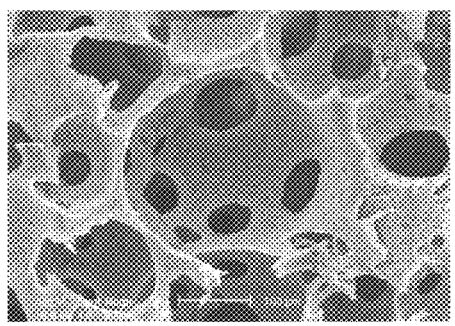
Figure 25D:
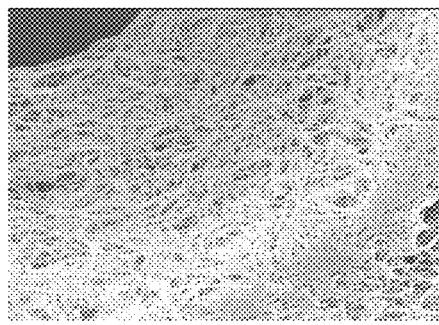
Figure 25E:
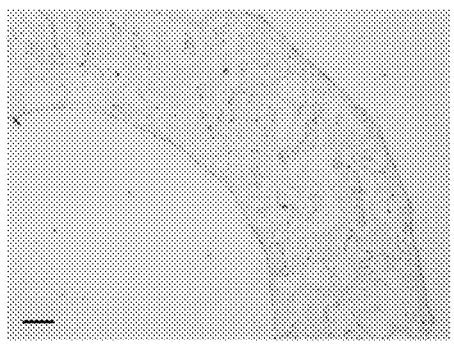
FIGS. 25E and 25F illustrate the histological analysis of in vitro cell cultures on the scaffolds of FIG. 25A (i.e., constructs) after 1 week, the constructs were stained with H-E and observed at low (E) and high (F) magnifications (scale bar: 200 μm)
Figure 25F:
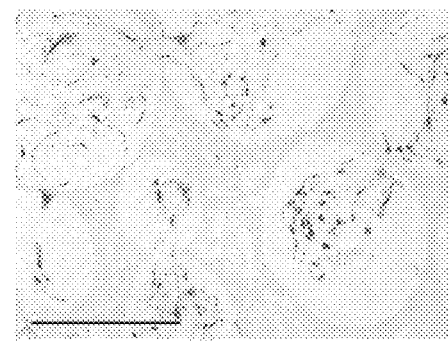

One example of the 3D tubular NF scaffold is shown in FIG. 25A. The scaffold had highly interconnected macro-pores (FIGS. 25B and 25C) and nano-scale fiber structure (FIG. 25D). The HASMCs were then seeded and cultured on the 3D tubular vascular scaffolds. Histological observation with H-E staining showed that the cells were distributed throughout the scaffolds after 1 week of in vitro culture (FIGS. 25E and 25F).

In Vitro Culture of HASMCs on Circular Disks of 3D Tubular NF Scaffolds

Figure 27:
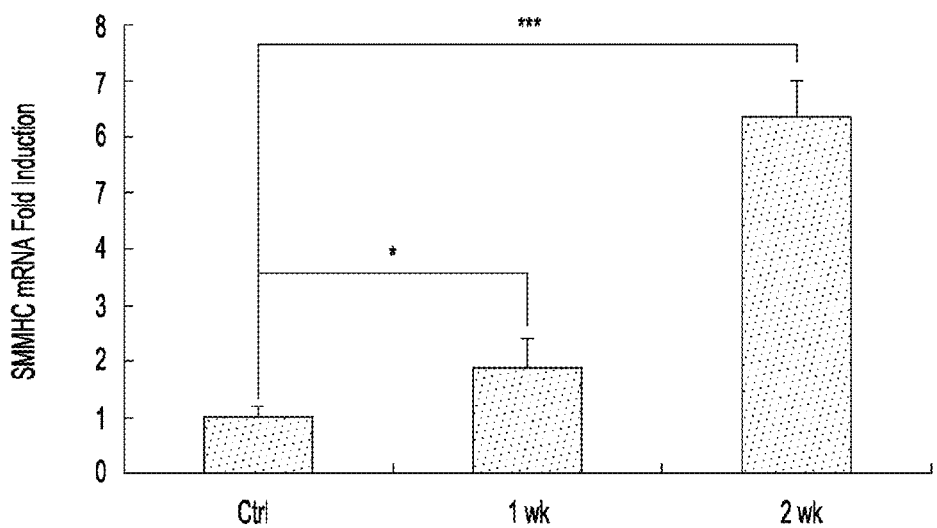
FIGS. 27 through 29 are graphs illustrating the gene expression of SMC specific markers on scaffolds compared to monolayer control cultures, * P<0.05,  P<0.01, *P<0.001.
Figure 26A:
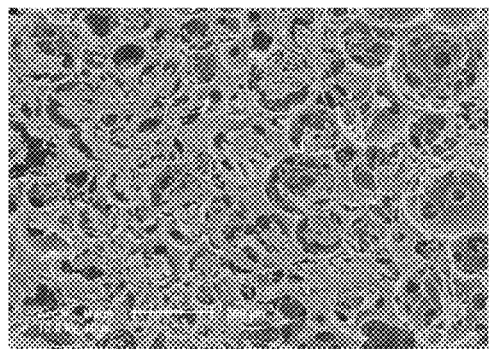
FIGS. 26A and 26B are SEM images of nano-fibrous cell-scaffold constructs after 24 hours of cell seeding and culture.
Figure 26B:
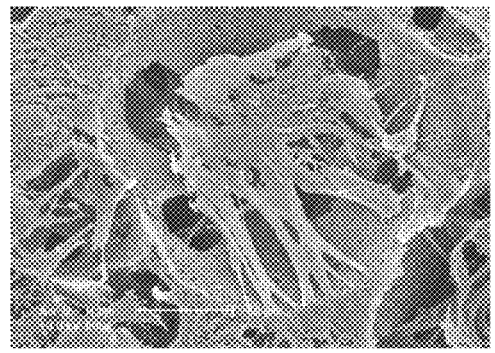
Figure 30A:
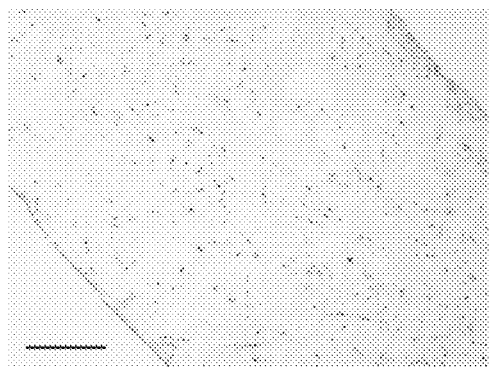
FIGS. 30A and 30B illustrate H-E staining (A) and Masson's trichrome staining (B) of sections of constructs cultured for 2 weeks (scale bar: 200 μm)
Figure 30B:
Figure 28:
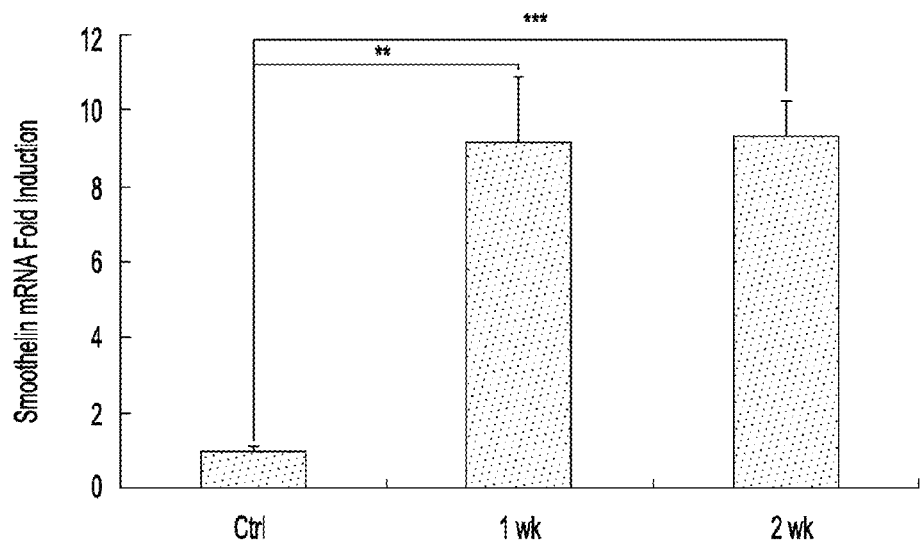
Figure 29:
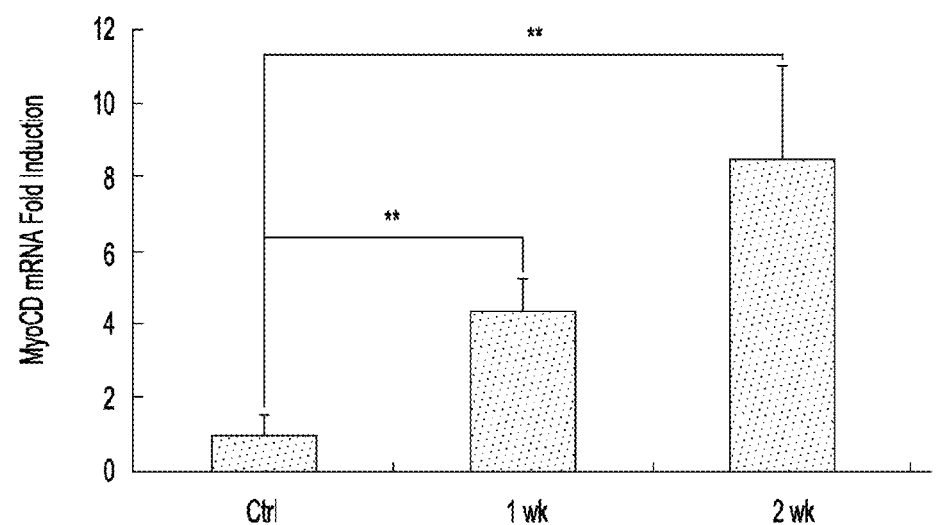

To investigate the scaffold-cell interaction, circular disk-shaped 3D NF scaffolds (3.6 mm in diameter and 1 mm in thickness) were used for HASMCs culture. The cells were seeded on scaffolds and cultured for 2 weeks. After 24 hours of cell seeding, the cells aggregated inside the pores of the scaffolds (FIGS. 26A and 26B). The expression levels of contractile phenotype marker genes were enhanced for cells cultured on 3D tubular NF scaffolds during the 2 weeks of culture, compared to monolayer control culture (FIGS. 27, 28 and 29), with elevated expression level of SMMHC, Smoothelin and MyoCD. H-E staining showed that the cells distributed throughout the whole scaffold after 2 weeks of culture (FIG. 30A); however, no significant collagen deposition was observed (FIG. 30B).

Subcutaneous Implantation of Scaffold-Cell Constructs

Figure 31A:
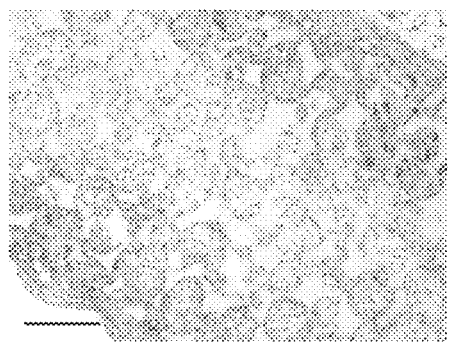
FIGS. 31A through 31F illustrate H-E staining of sections of constructs (A) and blank scaffolds (B) after 2 weeks of implantation, Masson's trichrome (C) staining of 2 week implants of constructs (collagenous ECM stained blue), immunohistochemical staining of IgG control 2 weeks after implantation (D), the donor and host derived SMCs stained with SM-α-actin antibody (E), and the donor-derived HASMCs stained with human mitochondria antibody (F) (scale bar: 200 μm)
Figure 31B:
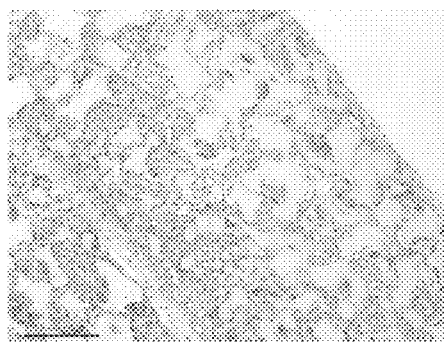
Figure 31C:
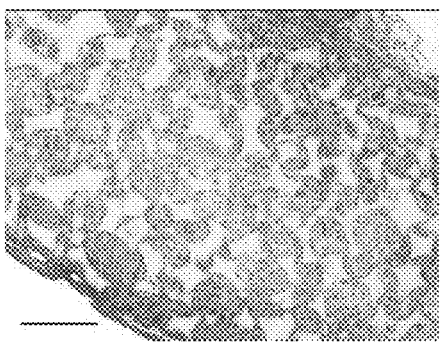
Figure 31D:
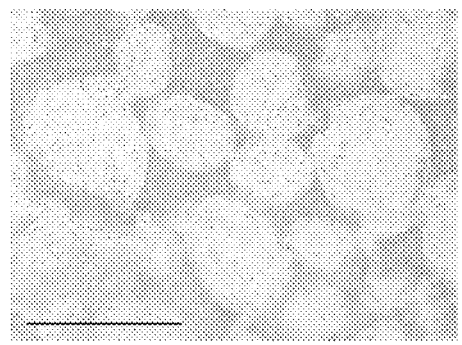
Figure 31E:
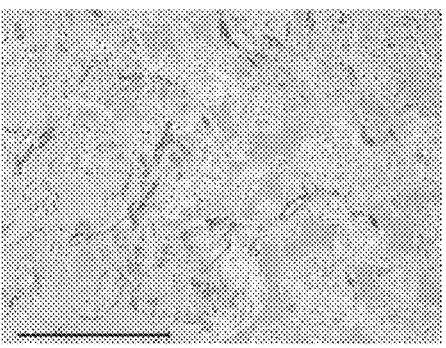
Figure 31F:
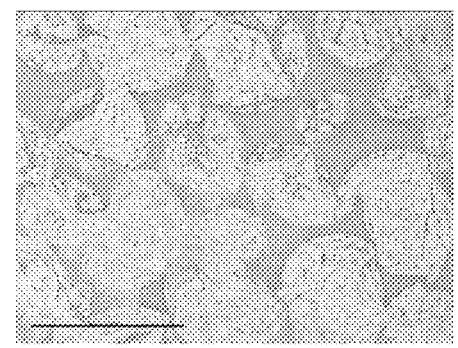

After the cells were seeded and cultured on the 3D tubular NF scaffolds for 24 hours, the scaffold-cell constructs or blank scaffolds were implanted into nude mice subcutaneously. After 2 weeks of implantation, the implants were collected and subjected to histological analysis. The tissue growth into the scaffolds was observed on both constructs (FIG. 31A) and blank scaffolds (FIG. 31B) implants. Collagen was deposited into the pores of constructs implants, shown by Masson's trichrome staining (FIG. 31C). While there was no staining for IgG control (FIG. 31D), positive staining of SMCs with antibody to SM-α-actin was observed in the implanted constructs (FIG. 31E). HASMCs remained in the constructs after 2 weeks of implantation, as shown by positive IHC staining with antibody to human mitochondria (FIG. 31F).

The 3D tubular NF scaffold modeled the blood vessel shape. With macro-pore design, the NF scaffold is able to support the growth and differentiation of SMCs. Synthetic phenotype SMCs are able to rapidly expand and deposit ECM, while contractile phenotype SMCs are able to contract or relax in response to vasoactive factors, leading to the blood vessel constriction or dilation. The PLLA NF matrices support SMCs with contractile phenotype, featured by more rounded cell shapes and higher expression of some contractile phenotype related marker genes. The cells distributed and grew well inside the 3D tubular NF scaffolds. Compared to monolayer culture, the expression levels of contractile phenotype related marker genes, including SMMHC, Smoothelin and MyoCD were all elevated, probably due to NF matrix and 3D culture conditions. As such, the nano-fiber matrix and 3D porous scaffolds are advantageous in terms of supporting implanted SMCs with contractile phenotype to reduce the risk of narrowing vessels. Likely due to the short time and poor environment of the in vitro culture, there was limited ECM deposition.

In vivo implantation of scaffold-cell constructs showed host tissue infiltration in the entire scaffolds. Significant collagen deposition inside the scaffolds was observed after 2 weeks of implantation. The implanted HASMCs remained in the scaffolds after 2 weeks of implantation. The results identified herein illustrate that the porous NF PLLA scaffolds favor a contractile phenotype of HASMCs.

Besides matrix effect, growth factors can greatly affect the cell proliferation and differentiation. It is believed that the controlled release of appropriated growth factors (using scaffolds) may allow for more precisely tailored phenotypes of SMCs along different development stages to engineer functional vascular grafts.

Example 5

In this example, a scaffold with a pore gradient was formed using a graded sugar sphere template.

Materials

Poly(l-lactic acid) (PLLA) with an inherent viscosity of 1.4-1.8 dl/g was used as received. d-fructose had a melting point ranging from 119° C. to 122° C.

Preparation of the Graded Sugar Sphere Template

Sugar spheres of different sizes were prepared by an emulsion technique. 100 mL of d-fructose was melted at 120° C. for 90 minutes until a clear yellowish liquid was obtained. The molten sugar was emulsified into 50 mL mineral oil with 1.3 mL sorbitanmonooleate (commercially available as Span 80 from Sigma) at 120° C. under stirring. The resulting mixture was cooled down using an ice-bath to solidify the sugar spheres. After discarding the mineral oil, the sugar spheres were washed with hexane three times and sieved to select desired sizes (into groups with sizes ranging from i) 125 μm to 250 μm, ii) 250 μm to 425 μm, and iii) 425 μm to 600 μm). The sieved sugar spheres were packed sequentially according to the sugar sphere size in a PTFE vial with hexane, and were heat treated at 37° C. for 30 minutes to form a sugar sphere template. After bonding the sugar spheres, hexane was removed, and the sugar template was dried under vacuum.

Polymer Casting and Phase Separation

From about 0.6 mL to about 0.8 mL of 10% PLLA/THF solution was cast into the assembled sugar template. Mild vacuum was applied during casting in order to fully fill the interspaces of the bonded sugar template with polymer solution. The polymer solution/sugar template was phase separated at −20° C. overnight and then immersed into cyclohexane to extract solvent (THF) for 2 days. The resulting composites were freeze-dried. The sugar template was then leached away in distilled water, and the highly porous nanofibrous scaffold was freeze-dried.

Structure/Property Characterization

Porous morphologies of the scaffolds were examined with scanning electron microscopy (SEM) (S-3200N, Hitachi, Japan). To expose the internal architecture, a sample was cut with a razor blade after freeze-drying. All samples were coated with gold using a sputter coater (Desk-II, Denton Vacuum Inc., Moorstown, N.J.) where the pressure was below 50 mTorr, the current was approximately 40 mA, and the coating time was 120 seconds. The overall porosity was calculated using the method described in Wei et al. "Structure and properties of nano-hydroxyapatite/polymer composite scaffolds for bone tissue engineering" *Biomaterials* 25 (19), pp. 4749-4757 (2004). The interpore opening size and interpore opening ratio (IOR) were determined from the SEM images according to Chen et al. "Nano-fibrous poly(L-lactic acid) scaffolds with interconnected spherical macropores" *Biomaterials*, 25 (11), pp. 2065-2073 (2004). The IOR is defined as the ratio of interpore opening area to the macropore surface area in a scaffold. At least 30 pores in a few representative SEM images were analyzed.

Graded Macropore Structure

Figure 33:
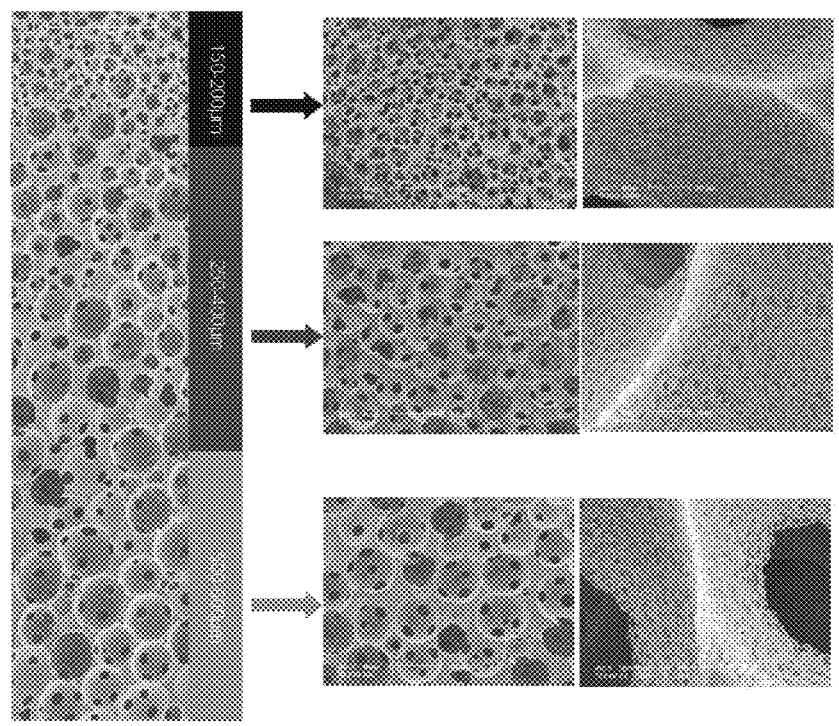
FIG. 33 includes SEM images illustrating the morphologies of the graded macropore structures of PLLA scaffolds formed using graded sugar templates.

FIG. 33 illustrates the macroporous and nano-fibrous scaffolds with a graded pore size formed using sugar template leaching and phase separation techniques. The results showed the typical morphology of scaffolds prepared using sugar spheres that were heat treated at 37° C. for 30 minutes (as described above). As shown in FIG. 33, the scaffold had a three-section graded pore structure with the average pore diameter respectively ranging from 125 µm to 250 µm (see top of gradient), from 250 µm to 425 µm (see middle of gradient), and from 425 µm to 600 µm (see bottom of gradient). The thickness of the three sections (i) 125 µm to 250 µm, ii) 250 µm to 425 µm, and iii) 425 µm to 600 µm) is 1 mm, 2 mm, and 2 mm, respectively. The thickness of the individual section can be easily controlled in the preparation of the sugar sphere template by adding different amounts of sugar spheres with different sizes. By varying the sugar sphere size, different macropore sizes can be achieved (see Table 4).

The three sections of the scaffold shown in FIG. 33 have almost the same high porosity of 98%, despite the differences in the macropore and interpore opening sizes. With the similar IOR of about 20%, the average interpore opening sizes are substantially graded, varying from 60 µm for the section prepared with 125 µm to 250 µm sugar spheres (see top of gradient) to 100 µm for the section prepared with 425 µm to 600 µm sugar spheres (see bottom of gradient). The IOR is controlled by the sugar sphere assembling conditions (e.g., assembling the different sugar sphere sizes under the same heat treatment temperature and time).

The nanofibers of the scaffold had an average diameter in the order of 100 nm.

TABLE 4

Structures of graded macroporous nano-fibrous scaffolds

| Macropre size (µm) | Porosity (%) | Average interpore opening size (µm) | Interpore opening area ratio (%) |
| --- | --- | --- | --- |
| 125-250 | 98.0 | 62 | 25.1% |
| 250-425 | 97.8 | 85 | 23.8% |
| 425-600 | 97.8 | 98 | 23.5% |

Scaffolds play a critical role in tissue engineering. The three-dimensional pore structure and surface morphology of the scaffolds affect the quality of the tissue being developed on the scaffold. The scaffolds disclosed herein are suitable for use as blood vessels, as well as many other tissues including nerves, muscles, tendons, ligaments, bone and teeth. As described herein, control over the architectural parameters (such as porosity, tubular diameter, and orientation direction of the microtubules) may be achieved by varying processing parameters, such as polymer concentration and temperature gradient. Moreover, by designing the molds using different materials for different parts, various oriented microtubules and gradient pore structures may be created. For example, a gradient scaffold can be created with the oriented structure from the outside wall (with larger pores) to the inside wall (with smaller pores). In this example, the inside layer with smaller pores could be advantageous for the seeding and growth of endothelial cells (ECs), while the outside layer with the bigger pores could create a more suitable environment for the growth of smooth muscle cells (SMCs) and their matrix synthesis. It is believed that the radially oriented microtubules within a scaffold provide an easier pathway for cell seeding and the uniform distribution throughout the scaffold. Cells can easily migrate into radially oriented tubular pores to achieve higher cell density and more uniform cell distribution throughout the scaffold than into the random pores of the control scaffold. The healthy appearance of the cells in the radially oriented pores may be associated with the better mass transfer conditions than in less interconnected pores of the control scaffold. The intact vessel-shaped geometry also demonstrates the adequate mechanical properties to support tissue regeneration in the ectopic implantation model. Furthermore, by simply controlling the ratio of solvents (e.g., benzene/THF), the polymer concentration and the phase separation temperature, scaffolds with different porosity, microtubule size, nano-fiber density on the microtubule walls can be created, allowing for the optimization of scaffolds for specific cells and specific tissues. Still further, a modified porogen template with a graded structure may be used to generate the desired controlled porous scaffold structure.

Each of the embodiments disclosed herein mimic the layered and/or gradient structure of natural tissue and organs. Different layers in a tissue may possess cell types or phenotypes that may be different from other layers, and these different cell types or phenotypes may require different environments, such as different macropore sizes and porosities. The scaffolds disclosed herein can advantageously be made to mimic the layered or gradient nature of these tissues and organs.

It is to be understood that the ranges provided herein include the stated range and any value or sub-range within the stated range. For example, a dimension ranging from about 2 µm to about 250 µm should be interpreted to include not only the explicitly recited amount limits of about 2 µm to about 250 µm, but also to include individual amounts, such as 10 µm, 50

µm, 220 µm, etc., and sub-ranges, such as 50 µm to 200 µm, etc. Furthermore, when "about" is utilized to describe a value, this is meant to encompass minor variations (up to +/−20%) from the stated value.

While several embodiments have been described in detail, it will be apparent to those skilled in the art that the disclosed embodiments may be modified. Therefore, the foregoing description is to be considered non-limiting.

What is claimed is:

1. A scaffold, comprising:
a tubular polymeric structure having: an outer cylindrical wall; and an inner cylindrical wall defining a longitudinal bore therethrough;
a controlled gradient of a plurality of solid-walled microtubules oriented radially between the outer cylindrical wall and the inner cylindrical wall in the tubular polymeric structure; and
a controlled gradient of a plurality of radially oriented microtubule pores, each pore defined between an adjacent pair of solid-walled microtubules;
wherein:
an average pore size of each of the plurality of microtubule pores decreases from the inner cylindrical wall of the tubular polymeric structure to the outer cylindrical wall of the tubular polymeric structure; or
an average pore size of each of the plurality of microtubule pores decreases from the outer cylindrical wall of the tubular polymeric structure to the inner cylindrical wall of the tubular polymeric structure;
and wherein the controlled gradients of the plurality of solid-walled microtubules and the plurality of radially oriented microtubule pores are formed using a multi-directional, radially oriented temperature gradient.

2. The scaffold as defined in claim 1 wherein:
a porosity of the scaffold ranges from about 89.3% to about 95.0% of a total volume of the scaffold;
the average pore size of each of the plurality of microtubule pores decreases from the inner cylindrical wall of the tubular polymeric structure to the outer cylindrical wall of the tubular polymeric structure; and
the average pore size adjacent the outer cylindrical wall is about 20 μm, and the average pore size adjacent the inner cylindrical wall is about 200 μm.

3. The scaffold as defined in claim 2 wherein a cross-section of each of the solid-walled microtubules is a polygon with a number of sides ranging from 3 to 7.

4. The scaffold as defined in claim 1 wherein:
a porosity of the scaffold ranges from about 89.3% to about 95.0% of a total volume of the scaffold;
the average pore size of each of the plurality of microtubule pores decreases from the outer cylindrical wall of the tubular polymeric structure to the inner cylindrical wall of the tubular polymeric structure; and
the average pore size adjacent the inner cylindrical wall is about 20 μm, and the average pore size adjacent the outer cylindrical wall is about 200 μm.

5. A method of making the scaffold as defined in claim 1, comprising:
pouring a polymer solution into a mold formed of at least two materials having different thermal conductivities such that the multi-directional, radially oriented temperature gradient can be formed in the mold;
exposing the mold and the polymer solution therein to a temperature ranging from −200° C. to 20° C. to form the multi-directional, radially oriented temperature gradient and to thermally induce phase separation of the polymer solution into a polymer/solvent system; and
freeze-drying the polymer/solvent system to form the scaffold having the tubular polymeric structure and the controlled gradient of solid-walled microtubules oriented radially therein;
wherein the mold is a cylinder having a cylinder wall formed of one of the at least two materials having different thermal conductivities, a removable top, a removable bottom, and an insertable shaft formed of another of the at least two materials having different thermal conductivities, and wherein pouring the polymer solution into the mold includes pouring the polymer solution in a space formed between the cylinder wall and the insertable shaft.

6. The method as defined in claim 5 wherein the removable top, the removable bottom, and the insertable shaft are each formed of the other of the at least two materials having different thermal conductivities, and wherein the other of the at least two materials has a lower conductivity than the one of the at least two materials having different thermal conductivities, and wherein the multi-directional, radially oriented temperature gradient is formed in a radial direction where a warmer portion of the temperature gradient is adjacent the insertable shaft and a colder portion of the temperature gradient is adjacent the cylinder wall.

7. The method as defined in claim 5 wherein the removable top, the removable bottom, and the insertable shaft are each formed of the other of the at least two materials having different thermal conductivities, and wherein the other of the at least two materials has a higher thermal conductivity than the one of the at least two materials having different thermal conductivities, and wherein the multi-directional, radially oriented temperature gradient is formed in a radial direction where a warmer portion of the temperature gradient is adjacent the cylinder wall and a colder portion of the temperature gradient is adjacent the insertable shaft.

8. The method as defined in claim 5, further comprising controlling at least one of a size of the solid-walled microtubules, a porosity of the scaffold, or an orientation of the solid-walled microtubules by at least one of i) altering a concentration of polymer in the polymer solution, ii) altering the temperature, or iii) altering the at least two materials of the mold.

* * * * *